US010519195B2

(12) United States Patent
Minakuchi

(10) Patent No.: US 10,519,195 B2
(45) Date of Patent: Dec. 31, 2019

(54) ANTIBODY PURIFICATION METHOD, ANTIBODY OBTAINED THEREFROM, NOVEL ANTIBODY PURIFICATION METHOD USING CATION EXCHANGER, AND ANTIBODY OBTAINED THEREFROM

(71) Applicant: KANEKA CORPORATION, Osaka (JP)

(72) Inventor: Kazunobu Minakuchi, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 489 days.

(21) Appl. No.: 15/022,890

(22) PCT Filed: Sep. 16, 2014

(86) PCT No.: PCT/JP2014/074452
§ 371 (c)(1),
(2) Date: Mar. 17, 2016

(87) PCT Pub. No.: WO2015/041218
PCT Pub. Date: Mar. 26, 2015

(65) Prior Publication Data
US 2016/0237113 A1    Aug. 18, 2016

(30) Foreign Application Priority Data

Sep. 17, 2013  (JP) ................... 2013-192378
Sep. 17, 2013  (JP) ................... 2013-192379

(51) Int. Cl.
*C07K 1/22*   (2006.01)
*C07K 1/36*   (2006.01)
*C07K 16/12*  (2006.01)

(52) U.S. Cl.
CPC ............ *C07K 1/22* (2013.01); *C07K 16/1271* (2013.01); *C07K 2317/55* (2013.01); *C07K 2317/622* (2013.01); *C07K 2317/626* (2013.01)

(58) Field of Classification Search
None
See application file for complete search history.

(56) References Cited

U.S. PATENT DOCUMENTS

| 3,932,557 A | 1/1976 | Matthews |
| 4,145,366 A * | 3/1979 | Ichikawa ............... C07C 45/67 549/498 |
| 4,210,723 A | 7/1980 | Dorman et al. |
| 4,772,653 A | 9/1988 | McKenna |
| 5,250,613 A | 10/1993 | Bergstrom et al. |
| 5,260,373 A | 11/1993 | Profy et al. |
| 5,516,675 A | 5/1996 | Uchida et al. |
| 5,874,165 A | 2/1999 | Drumheller |
| 6,399,750 B1 | 6/2002 | Johansson |
| 8,101,425 B1 | 1/2012 | Carbonell |
| 9,890,191 B2 * | 2/2018 | Minakuchi ............ C07K 1/165 |
| 2004/0224338 A1 | 11/2004 | Chicz et al. |
| 2005/0143566 A1 | 6/2005 | Hober |
| 2006/0160064 A1 | 7/2006 | Carbonell |
| 2006/0194950 A1 | 8/2006 | Hober et al. |
| 2006/0194955 A1 | 8/2006 | Hober et al. |
| 2007/0112178 A1 | 5/2007 | Johansson et al. |
| 2007/0167613 A1 | 7/2007 | Johansson et al. |
| 2007/0207500 A1 * | 9/2007 | Bian ................. B01D 15/3809 435/7.1 |
| 2007/0213513 A1 * | 9/2007 | Van Alstine ....... B01D 15/1864 530/416 |
| 2007/0244307 A1 | 10/2007 | Engstrand et al. |

(Continued)

FOREIGN PATENT DOCUMENTS

EP    1 352 957 A1    10/2003
EP    2 027 921 A2    2/2009

(Continued)

OTHER PUBLICATIONS

Liu et al. "Revoery and purificaiton process development for monoclonal antibody production" mAbs 2:5, 480-499 (Year: 2010).*
Extended European Search Report dated Mar. 21, 2017 in Patent Application No. 14846521.4.
Sophia Hober, et al., "Protein a chromatography for antibody purification", Journal of Chromatography B, 2007, vol. 848, pp. 40-47.
Duncan Low, et al., "Future of antibody purification", Journal of Chromatography B, 2007, vol. 848, pp. 48-63.
Ana C.A. Roque, et al., "Affinity-based methodologies and ligands for antibody purification Advances and perspectives" Journal of Chromatography A, 2007, vol. 1160, pp. 44-55.
Takeo Yamabe et al., "Kongo Ion Kokan Column ni yoru Amino Acid no Gunbunri", Journal of the Chemical Society of Japan, 1968, vol. 89 No. 8, pp. 772-775 (with partial English translation).

(Continued)

*Primary Examiner* — Daniel E Kolker
*Assistant Examiner* — James L Rogers
(74) *Attorney, Agent, or Firm* — Oblon, McClelland, Maier & Neustadt, L.L.P.

(57) ABSTRACT

The first embodiment of the present invention is a method for purifying an antibody or a substance derive from an antibody, wherein a carrier 1 having an affinity ligand with affinity for the antibody or the substance derived from the antibody and a carrier 2 having a cation exchange group are used to prepare an integrated column 1 connecting a column containing the carrier 1 and a column containing the carrier 2 or a column 2 having the mixture of the carrier 1 and carrier 2, the antibody or the substance derived from the antibody is applied to the column 1 or the column 2, and then the adsorbed antibody or substance derived from the antibody is eluted from the column 1 or the column 2. The second embodiment of the present invention is a method for using a carrier having a cation exchange group, wherein a solution containing an antibody or a substance derived from an antibody is applied to a carrier having a cation exchange group having a carboxyl group-containing ligand and pKa of 4.0 or more, and the antibody or the substance derived from the antibody is eluted by an acidic buffer having pH of 4.0 or less.

21 Claims, 8 Drawing Sheets

(56) References Cited

U.S. PATENT DOCUMENTS

| | | |
|---|---|---|
| 2007/0259453 A1 | 11/2007 | Engstrand et al. |
| 2008/0167450 A1 | 7/2008 | Pan |
| 2008/0177048 A1 | 7/2008 | Gagnon |
| 2009/0050566 A1 | 2/2009 | Kozlov et al. |
| 2009/0098660 A1 | 4/2009 | Falkenstein et al. |
| 2009/0105465 A1 | 4/2009 | Arunakumari et al. |
| 2009/0171072 A1 | 7/2009 | Alfonso et al. |
| 2009/0247735 A1 | 10/2009 | Gagnon |
| 2009/0270596 A1 | 10/2009 | Gagnon et al. |
| 2010/0022760 A1 | 1/2010 | Hober et al. |
| 2010/0063261 A1 | 3/2010 | Bian et al. |
| 2010/0135987 A1 | 6/2010 | Hickman et al. |
| 2010/0145029 A1 | 6/2010 | Gagnon |
| 2010/0200507 A1 | 8/2010 | Kozlov et al. |
| 2010/0234577 A1 | 9/2010 | Mazzola et al. |
| 2010/0316645 A1 | 12/2010 | Imhof-Jung et al. |
| 2011/0065901 A1 | 3/2011 | Soice et al. |
| 2011/0073548 A1* | 3/2011 | Williams ............... G01N 30/28 210/739 |
| 2011/0105730 A1 | 5/2011 | Bian et al. |
| 2011/0112276 A1 | 5/2011 | Hober |
| 2011/0118442 A1 | 5/2011 | Engstrand et al. |
| 2011/0139717 A1 | 6/2011 | Malenfant et al. |
| 2011/0144311 A1 | 6/2011 | Chmielowski et al. |
| 2011/0206687 A1 | 8/2011 | Hickman |
| 2011/0251374 A1 | 10/2011 | Suenaga et al. |
| 2011/0263823 A1 | 10/2011 | Gagnon |
| 2011/0266225 A1 | 11/2011 | Johansson et al. |
| 2011/0284446 A1 | 11/2011 | Kozlov et al. |
| 2011/0288277 A1 | 11/2011 | Kozlov et al. |
| 2012/0121819 A1 | 5/2012 | Kozlov et al. |
| 2012/0129150 A1 | 5/2012 | Carbonell |
| 2012/0165511 A1 | 6/2012 | Arunakumari et al. |
| 2012/0193278 A1 | 8/2012 | Kozlov et al. |
| 2012/0238724 A1 | 9/2012 | Hober |
| 2012/0264915 A1 | 10/2012 | Gagnon et al. |
| 2013/0096276 A1 | 4/2013 | Yoshida et al. |
| 2013/0184438 A1 | 7/2013 | Hober et al. |
| 2013/0260419 A1* | 10/2013 | Ransohoff ............ C12M 47/10 435/69.6 |
| 2013/0287771 A1 | 10/2013 | Hickman |
| 2014/0179904 A1 | 6/2014 | Arunakumari et al. |
| 2014/0243508 A1 | 8/2014 | Falkenstein et al. |
| 2014/0255423 A1 | 9/2014 | Hickman et al. |
| 2015/0073128 A1 | 3/2015 | Engstrand et al. |
| 2015/0210735 A1 | 7/2015 | Hickman et al. |
| 2015/0225445 A1 | 8/2015 | Minakuchi |
| 2016/0083454 A1* | 3/2016 | Duthe ................. C07K 16/065 530/388.26 |
| 2016/0130339 A1 | 5/2016 | Hickman |

FOREIGN PATENT DOCUMENTS

| | | |
|---|---|---|
| JP | 05-202098 A | 8/1993 |
| JP | 06-228200 A | 8/1994 |
| JP | 2002-522779 A | 7/2002 |
| JP | 2008-502920 A | 1/2008 |
| JP | 2008-505851 A | 2/2008 |
| JP | 2008-535913 A | 9/2008 |
| JP | 2008-542218 A | 11/2008 |
| JP | 43-91830 A | 12/2009 |
| JP | 2010-507583 A | 3/2010 |
| JP | 2010-510963 A | 4/2010 |
| JP | 2010-517942 A | 5/2010 |
| JP | 2010-133733 A | 6/2010 |
| JP | 2010-133734 A | 6/2010 |
| JP | 2011-517462 A | 6/2011 |
| JP | 2011-256176 A | 12/2011 |
| JP | 2012-530088 A | 11/2012 |
| JP | 2013-501721 A | 1/2013 |
| WO | WO-9957134 A1 * | 11/1999 ............... C07K 1/18 |
| WO | WO 2004/074471 A1 | 9/2004 |
| WO | WO 2005/082483 A1 | 9/2005 |
| WO | WO 2005/082926 A1 | 9/2005 |
| WO | WO 2006/043895 A1 | 4/2006 |
| WO | 2008-085988 A1 | 7/2008 |
| WO | WO 2009/058769 A1 | 5/2009 |
| WO | 2010/019493 A1 | 2/2010 |
| WO | WO 2010/071208 A1 | 6/2010 |
| WO | 2010/141039 A1 | 12/2010 |
| WO | WO 2011/017514 A1 | 2/2011 |
| WO | WO-2011017514 A1 * | 2/2011 ............... C07K 1/36 |
| WO | WO 2011/050071 A2 | 4/2011 |
| WO | WO 2011/081898 A1 | 7/2011 |
| WO | WO 2011/118699 A1 | 9/2011 |
| WO | 2014/034457 A1 | 3/2014 |

OTHER PUBLICATIONS

Chunyan Hou, et al., "Weak anion and cation exchange mixed-bed microcolumn for protein separation", J. Sep. Sci., 2010, vol. 33, pp. 3299-3303.

International Search Report dated Dec. 22, 2014 for PCT/JP2014/074452 filed on Sep. 16, 2014.

Extended European Search Report dated Dec. 17, 2015 in Patent Application No. 13833630.0, 7 pages.

Pete Gagnon, "Technology Trends in Antibody Purification" Journal of Chromatography A, vol. 1221, XP055027826, Jan. 1, 2012, pp. 57-70.

Pete Gagnon, et al., "Cooperative Multimodal Retention of IgG, Fragments, and Aggregates on Hydroxyapatite" Journal of Separation Science, vol. 32, No. 22, XP055235544, Nov. 1, 2009, pp. 3857-3865.

Greg T. Hermanson, et al., Immobilized Affinity Ligand Techniques Academic Press, 1992, pp. 51-136 and Cover page.

Charlotta Ljungquist, et al., "Thiol-Directed Immobilization of Recombinant IgG-Binding Receptors" Eur. J. Biochem. vol. 186, 1989, pp. 557-561.

Martin Lackmann, et al., "Purification and Structural Analysis of a Murine Chemotactic Cytokine (CP-10) with Sequence Homology to S100 Proteins" The Journal of Biological Chemistry, vol. 267, No. 11, 1992, pp. 7499-7504.

"Ion Exchange Resin and Its Technology and its Application (Basic)" Revision 2, Organo Corporation, Mar. 31, 1997 pp. 10, 11, 24-27 (with partial English translation).

"Diaion (R) 1" Revision 4, Mitsubishi Chemical Corporation, Oct. 31, 2007, pp. 4, 5, 8 and 9 (with partial English translation).

* cited by examiner

ANTIBODY PURIFICATION METHOD, ANTIBODY OBTAINED THEREFROM, NOVEL ANTIBODY PURIFICATION METHOD USING CATION EXCHANGER, AND ANTIBODY OBTAINED THEREFROM

TECHNICAL FIELD

The first embodiment of the present invention relates to a novel method for purifying a target molecule in which a carrier having an affinity ligand for specifically purifying the target molecule (for example, an antibody or a substance derived from an antibody, hereinafter these are referred to as antibodies in some cases) and a carrier having a cation exchange group at the same time, and the purifications of the affinity chromatography and the cation exchange chromatography are performed at one chromatography step, and an antibody obtained therefrom.

In addition, the second embodiment of the present invention relates to a novel method for purifying antibodies (an antibody or a substance derived from an antibody) in which a cation exchange group (hereinafter, referred to as a carrier having a cation exchange group or a cation exchange carrier) is used at pH of 4.0 or less which conventionally has not been selected as pH of a cation exchange carrier having a carboxyl group as a ligand, and an antibody obtained therefrom.

BACKGROUND ART

A monoclonal antibody as active pharmaceutical ingredients of an antibody drug containing an antibody as a main component is mainly expressed in a culture fluid as a recombinant protein using a mammalian cultured cell or the like, and purified to a high purity by several steps of chromatography and filtration process before formulation.

An antibody drug includes not only a molecule generally called an antibody such as immunoglobulin G and an analog thereof, but also an Fc fusion protein (Fc-containing molecule) in which an Fc region of a constant region of an immunoglobulin molecule is fused to another functional protein or peptide. Further, antibody drugs include low-molecular antibodies such as Fab, scFv, and diabody. Antibody drugs are also prepared by purifying and formulating from recombinant microorganisms, secreted substances in the culture supernatant, or expressed substances in bacterial cell or periplasmic space.

Impurities such as aggregates of antibodies (a dimeric and multiple form of a monomer) which are formed or remains in the steps of culture, purification and formulation is a major cause of side effects, and it is an important issue to reduce the impurities on production of an antibody preparation. Here, a monomer is defined as a unit of a molecule of an antibody having a tetramer structure composed of two molecules of heavy chains (H chains) consisting of an Fc region of a constant region, and a variable region, and two molecules of light chains (L chains) consisting of a variable region. A multimer of the unit molecules is regarded as an aggregate, and thought to be a major cause of side effects of an antibody preparation.

Attempts to control suppression of production of the aggregate and remove the aggregate have been made by a complicated management technique and use of an additive in the steps of culture, purification and formulation. Especially, not only suppression of production of the aggregate, but also removal of the aggregate is important in the purification step. Thus, development of a simple and efficient technique for removing the aggregate has been required in the purification step.

Patterning of purification techniques by combining particular unit operations (making of a platform) is developed in the purification step of the antibody preparation. In the early purification step (recovery step), an antibody affinity separation matrix in which protein A is immobilized as a ligand on a water-insoluble carrier (protein A carrier) is widely utilized. A technique of adsorbing an antibody to the protein A carrier under neutral conditions, and eluting the antibody under acidic conditions is generally used. In general, the antibody is purified at high purity with three chromatography steps, and impurities such as an aggregate are removed by a combination of ion exchange chromatography, hydrophobic interaction chromatography and the like, in the subsequent step of protein A chromatography step (Non-patent Document 1, Non-patent Document 2, Non-patent Document 3, Patent Document 5).

An affinity ligand has a function of specifically binding to a particular molecule, and an affinity separation matrix (hereinafter referred to as affinity chromatography carrier, or affinity carrier) prepared by immobilizing the ligand to a water-insoluble carrier is utilized for efficient separation and purification of a useful substance from biological components or recombinant cell culture including microorganisms and mammalians. An industrially utilized antibody affinity ligand includes, for example, a peptide ligand or a protein ligand derived from a microorganism such as protein A, protein G and protein L or consisted of a functional variant (analog substance) obtained by recombinant technology thereof; a recombinant protein ligand such as a camel single strand antibody and an Fc receptor of an antibody; and a chemosynthetic ligand such as a thiazole derivative. The antibody affinity ligand is used in purification of an antibody drug and the like. Since the antibody preparation has lower toxicity and higher specificity than chemicals, there is much demand for an antibody drug as an ideal pharmaceutical.

In the separation and purification of antibodies from the affinity carrier, there is a problem to remove the aggregate of antibodies, impurities from host, and degradation products of the antibody (hereinafter referred to as aggregates and the like).

For example, the protein A chromatography step is generally carried out with acidic elution in one example of an affinity carrier. However, since the process design thereof takes much time due to the requirement of different elution pH every antibody and the lower the elution pH is, the more the risk of formation of an aggregate is, the protein A ligand is modified by means of protein engineering, so that the antibody which requires pH elution as low as about pH 3 can also be eluted near pH 3.5 to 4 (Patent Document 1).

Moreover, after protein A chromatography step, high content of the aggregate is resulted in lowering of yield of the objective monomeric substance (monomer) in the subsequent step of removing impurities. Thus, not only suppression of the formation of an aggregate, but also removal of an aggregate is studied in the protein A chromatography step.

In addition, a method for decreasing impurities such as aggregates is examined in the protein A chromatography step. That is to say, optimization of pH and ionic strength at the time of elution, as well as fractionation of the first half of the elution peak and the second half of the elution peak, and the like are proposed.

Concretely, there are methods utilizing slight decrease of dissociation constant by contacting an antibody molecule polymerized with a protein A ligand with higher frequency than that of an antibody molecule which is not polymerized as a characteristic of the protein A carrier, and utilizing separation mechanisms based on delicate adjustment of hydrophobicity (Patent Document 2, Patent Document 3, Patent Document 4). However, since these methods are difficult to be strictly controlled and have low resolution, these methods are not used as a general separation technique, and the removal of impurities is required in the subsequent steps.

The affinity chromatography represented by protein A chromatography uses an acidic pH for elution, and the subsequent ionic exchange chromatography and hydrophobic interaction chromatography and the like generally use pH of 5.0 or more, so that the adjustments of pH and ionic strength are required.

On the other hand, the cation exchange carrier is generally used at higher pH than pKa of a ligand thereof. The adsorption and desorption to the cation exchange carrier for a target protein is performed at lower pH than isoelectric point (pI) of the protein. For example, in the purification of antibodies having pI of 8, the cation exchange carrier having a sulfone group having pKa of about 2 or a carboxyl group having pKa of about 3 to 5 as a ligand is used both with the buffer having pH of 5 to 6 to adsorb and desorb for the purification of target proteins. The pH of the buffer is set between pKa of the ligand and pI of the target proteins. In the case where the used pH is far lower than pI, the positive charge of the proteins is increased, and high ionic strength is necessarily set for the elution, so that it is likely to decrease the recovery. In the case where the ionic strength of the eluate is high, the ionic strength sometime has to be decreased in the subsequent process constructions. In addition, when the used pH is near or lower than pKa of the cation exchange ligand, the negative charge of the ligand is protonated and the binding capacity of the ligand is decreased, so that such low pH range generally has not been selected. Therefore, the buffer having pH of 5 to 6 has been used for the cation exchange carrier having pKa of 2 to 5 in the purification of antibodies using the cation exchange carrier.

Not only when the anion exchange chromatography step or the hydrophobic interaction chromatography step is used after the affinity chromatography step (Patent Document 8), but also when the anion exchange chromatography step is performed after the cation exchange chromatography (Patent Document 7) or the multiple target substances are collected at the cation exchange chromatography step (Patent Document 6), the adjustments of pH and ionic strength have been required.

In the case where the antibodies and the like are purified with the affinity chromatography and are further purified at high degree in the subsequent processes, the adjustments of pH and ionic strength of acidic eluate are required and there are limitations for the efficiency of continuous chromatographies initialized. In addition, even when the ionic exchange chromatography step and the hydrophobic charge induction chromatography step are performed without using the affinity chromatography purification, there were limitations for the efficiency that each step must be performed independently and the antibodies cannot be purified continuously (Patent Document 9).

In addition, although the antibody affinity separation matrix exhibits high specificity to an antibody and can collect the antibody at high purity, the ability of separating a monomeric substance (monomer) and an aggregate and the like is low even if the usage is strictly set. Thus, the antibody affinity separation matrix had limitation for removing an aggregate.

PRIOR ART

Patent Document

Patent Document 1: JP 4391830
Patent Document 2: WO 2008/085988
Patent Document 3: JP 2010-507583
Patent Document 4: WO 2010/019493
Patent Document 5: WO 2010/141039
Patent Document 6: JP H05-202098
Patent Document 7: JP H06-228200
Patent Document 8: JP 2010-510963
Patent Document 9: JP 2008-535913

Non-Patent Document

Non-Patent Document 1: Hober S. et al., J. Chromatogr. B, 2007, Vol. 848, pages 40-47
Non-Patent Document 2: Low D. et al., J. Chromatogr. B, 2007, Vol. 848, pages 48-63
Non-Patent Document 3: Roque A. C. A. et al., J. Chromatogr. A, 2007, Vol. 1160, pages 44-55

SUMMARY OF THE INVENTION

Problems to be Solved by the Invention

An object of the first embodiment of the present invention is to provide a novel method for purifying an antibody which, in a first chromatography step of a process for purifying an antibody or an Fc-containing molecule or a substance derived from an antibody such as low molecular antibodies such as Fab, scFv, can improve the purity of the antibody as the main target substance of the affinity purification, and can also improve the selective separation properties of monomers, and can reduce or omit the burden on a subsequent impurity removal step with respect to the removal of impurities such as aggregates.

The subject of the second embodiment of the present invention is to provide an efficient method for purifying an antibody, in which the affinity chromatography purification is used as collective chromatography step in the purification of the antibodies and the like, without requiring the adjustments of pH and the ionic strength of the acidic eluate which has been required for the purification at the high degree in the subsequent processes.

Solutions to the Problems

The present inventor has found a novel separation technique having a specific adsorption capacity and the excellent removal ability of aggregates and the like by packing a carrier having an affinity ligand with affinity for an antibody or a substance derived from an antibody and a carrier having a cation exchange group in the same column or the connecting column to perform simultaneously both the affinity chromatography and the cation exchange chromatography, to complete the first embodiment of the present invention.

In addition, the present inventor has found a novel separation technique for a cation exchange carrier obtaining a fraction having decreased impurities such as aggregates of the antibody, by adsorbing and desorbing antibodies and the like on the cation exchange carrier at acidic pH for eluting an antibodies from an antibody affinity carrier, to complete the second embodiment of the present invention.

In other words, the gist of the first embodiment of the present invention is as follows:

[1] A method for purifying an antibody or a substance derived from an antibody, wherein a carrier 1 having an affinity ligand with affinity for the antibody or the substance derived from the antibody and a carrier 2 having a cation exchange group are used to prepare an integrated column 1 connecting a column containing the carrier 1 and a column containing the carrier 2 or a column 2 having a mixture of the carrier 1 and the carrier 2, the antibody or the substance derived from the antibody is applied to the column 1 or the column 2, and then the adsorbed antibody or substance derived from the antibody is eluted from the column 1 or the column 2.

[2] A method for purifying an antibody or a substance derived from an antibody with a carrier 1 having an affinity ligand with affinity for the antibody or the substance derived from the antibody and a carrier 2 having a cation exchange group, wherein a solution containing the antibody or the substance derived from the antibody is applied to an integrated column 1 connecting a column containing the carrier 1 and a column containing the carrier 2 in series or a column 2 having a mixture of the carrier 1 and the carrier 2, and an eluate is passed through the integrated column or the mixed column to elute the adsorbed antibody or the substance derived from the antibody.

[3] The method according to [1] or [2], wherein the antibody or the substance derived from the antibody is eluted by the eluate having an acidic pH with an ionic strength linear gradient.

[4] The method according to [1] or [2], wherein the antibody or the substance derived from the antibody is eluted by the eluate having an acidic pH with an ionic strength step gradient.

[5] The method according to any one of [2] to [4], wherein
the integrated column or the mixed column is equilibrated with an equilibration buffer, the solution containing the antibody or the substance derived from the antibody is applied to the integrated column or the mixed column, and the integrated column or the mixed column is washed with a wash buffer having higher pH than that of the eluate and lower ionic strength than those of the equilibration buffer and the solution containing the antibody or the substance derived from the antibody before elution.

[6] The method according to any one of [2] to [4], wherein
the integrated column or the mixed column is equilibrated with an equilibration buffer, the solution containing the antibody or the substance derived from the antibody is applied to the integrated column or the mixed column, the integrated column or the mixed column is washed with a washing buffer 1 having higher pH than that of the eluate and ionic strength greater than or equal to those of the equilibration buffer and the solution containing the antibody or the substance derived from the antibody, and is washed with a washing buffer 2 having higher pH than that of the eluate and lower ionic strength than those of the equilibration buffer and the solution containing the antibody or the substance derived from the antibody before elution.

[7] The method according to any one of [1] to [6], wherein the carrier 1 has protein A, protein G, protein L or an analog thereof as a ligand.

[8] The method according to any one of [1] to [7], wherein the carrier 1 has protein A or an analog thereof as a ligand.

[9] The method according to any one of [1] to [8], wherein the antibody or the substance derived from the antibody is immunoglobulin G, immunoglobulin G derivative, or Fc-containing molecule.

[10] The method according to any one of [1] to [9], wherein the antibody or the substance derived from the antibody is Fab, scFv, diabody, or a molecule containing a binding part to an antigen.

[11] The method according to any one of [1] to [10], wherein the carrier 2 has a carboxyl group as a ligand.

[12] The method according to [11], wherein the carboxyl group is derived from an acidic amino acid.

[13] The method according to any one of [1] to [12], wherein the elution pH of the antibody or the substance derived from the antibody is less than 5.0.

[14] The method according to any one of [1] to [13], wherein dynamic binding capacity at 10% break through (10% DBC) of the carrier 1 to IgG at 6 minutes of contact time is 1 mg/mL or more and 100 mg/mL or less.

[15] The method according to any one of [1] to [14], wherein the carrier 2 has the ion exchange capacity of 0.001 mmol/mL or more and 0.5 mmol/mL or less.

[16] The method according to any one of [1] to [15], wherein the carrier 1 has the volume average particle diameter of 1 μm or more and 1000 μm or less, and the carrier 2 has the volume average particle diameter of 1 μm or more and 1000 μm or less.

[17] The method according to any one of [1] to [16], wherein
the solution containing the antibody or the substance derived from the antibody is applied to the carrier 2 having a cation exchange group having a carboxyl group-containing ligand and pKa of 4.0 or more, and the antibody or the substance derived from the antibody is eluted by an acidic buffer having pH of 4.0 or less.

[18] The method according to any one of [1] to [17], wherein 10% DBC of the carrier 2 to IgG at 6 minutes of contact time is 1 mg/mL or more and 200 mg/mL or less.

[19] The method according to any one of [2] to [18], wherein
the column packed with the carrier 1 having an affinity ligand is connected to the column packed with the carrier 2 having the cation exchange group such that the column packed with the carrier 2 is downstream to prepare the integrated column, the solution containing the antibody or the substance derived from the antibody is applied to the integrated column under condition of neutral pH, and the antibody or the substance derived from the antibody is eluted by an acidic buffer having pH of 4.0 or less.

[20] The method according to any one of [2] to [19], wherein the ratio of the carrier 1 to the carrier 2 of the integrated column is 1/20 or more and 20/1 or less on the basis of the volume.

[21] The method according to any one of [2] to [18], wherein
the carrier 1 having an affinity ligand is mixed with the carrier 2 having a cation exchange group to prepare the mixed column, the solution containing the antibody or the substance derived from the antibody is applied to the mixed column under condition of neutral pH, and the antibody or the substance derived from the antibody is eluted by an acidic buffer having pH of 4.0 or less.

[22] The method according to any one of [2] to [18] and [21], wherein the ratio of the carrier 1 to the carrier 2 of the mixed column is 1/20 or more and 20/1 or less on the basis of the volume.

[23] The method according to any one of [1] to [22], wherein the ratio of 10% DBC of the carrier 2 to IgG at 6 minutes of contact time relative to 10% DBC of the carrier 1 to IgG at 6 minutes of contact time under each adsorption condition is 1/10 times or more and 10 times or less.

[24] An antibody or a substance derived from an antibody purified with the method according to any one of [1] to [23].

The gist of the second embodiment of the present invention is as follows:

[1] A method for using a carrier having a cation exchange group, wherein
a solution containing an antibody or a substance derived from an antibody is applied to a carrier 2 having a cation exchange group having a carboxyl group-containing ligand and pKa of 4.0 or more, and
the antibody or the substance derived from the antibody is eluted by an acidic buffer having pH of 4.0 or less.

[2] The method according to [1], wherein the carboxyl group-containing ligand is derived from an acidic amino acid.

[3] The method according to [1] or [2], wherein 10% DBC of the carrier 2 to IgG at 6 minutes of contact time is 1 mg/mL or more and 200 mg/mL or less.

[4] The method according to any one of [1] to [3], wherein the carrier 2 has the ion exchange capacity of 0.001 mmol/mL or more and 0.5 mmol/mL or less.

[5] The method according to any one of [1] to [4], wherein the carrier 2 has the volume average particle diameter of 1 μm or more and 1000 μm or less.

[6] The method according to any one of [1] to [5], wherein
a column packed with a carrier 1 having an affinity ligand is connected to a column packed with the carrier 2 having the cation exchange group such that the column packed with the carrier 2 is downstream to prepare an integrated column,
the solution containing the antibody or the substance derived from the antibody is applied to the integrated column under condition of neutral pH, and
the antibody or the substance derived from the antibody is eluted by an acidic buffer having pH of 4.0 or less.

[7] The method according to any one of [1] to [5], wherein
the carrier 1 having an affinity ligand is mixed with the carrier 2 having the cation exchange group to prepare a mixed column,
the solution containing the antibody or the substance derived from the antibody is applied to the mixed column under condition of neutral pH, and
the antibody or the substance derived from the antibody is eluted by an acidic buffer having pH of 4.0 or less.

[8] The method according to [6] or [7], wherein
the integrated column or the mixed column is equilibrated with an equilibration buffer,
the solution containing the antibody or the substance derived from the antibody is applied to the integrated column or the mixed column, and
the integrated column or the mixed column is washed with a washing buffer having higher pH than that of an eluate and lower ionic strength than those of the equilibration buffer and the solution containing the antibody or the substance derived from the antibody before elution.

[9] The method according to [6] or [7], wherein
the integrated column or the mixed column is equilibrated with an equilibration buffer,
the solution containing the antibody or the substance derived from the antibody is applied to the integrated column or the mixed column,
the integrated column or the mixed column is washed with a washing buffer 1 having higher pH than that of an eluate and ionic strength greater than or equal to those of the equilibration buffer and the solution containing the antibody or the substance derived from the antibody, and a washing buffer 2 having higher pH than that of the eluate and lower ionic strength than those of the equilibration buffer and the solution containing the antibody or the substance derived from the antibody before elution.

[10] The method according to any one of [1] to [9], wherein the antibody or the substance derived from the antibody is immunoglobulin G, immunoglobulin G derivative, Fc-containing molecule, Fab, scFv, diabody, or a molecule containing a binding part to an antigen.

[11] The method according to any one of [1] to [10], wherein the antibody or the substance derived from the antibody is eluted by the eluate having an acidic pH with an ionic strength linear gradient.

[12] The method according to any one of [1] to [10], wherein the antibody or the substance derived from the antibody is eluted by the eluate having an acidic pH with an ionic strength step gradient.

[13] An antibody or a substance derived from an antibody purified with the method according to any one of [1] to [12].

Effects of the Invention

According to the first embodiment of the present invention, in the first affinity chromatography step of a process for purifying an antibody, Fc-containing molecule, or a substance derived from an antibody such as small molecular antibodies such as Fab, scFv, the antibody as the main target substance of the affinity purification can be purified at high purity, the selective separation properties of monomers can also be improved; and the burden on a subsequent impurity removal step can be reduced.

According to the second embodiment of the present invention, after the affinity chromatography step of the first step of the purification of the antibodies and the like, the efficient process can be constructed such that the affinity chromatography purification and the cation exchange chromatography purification can be performed in an integrated manner, by treating the eluate with the cation exchange chromatography as it is or by adsorbing and desorbing the antibodies and the like on the cation exchange carrier at the same pH as that of acidic elution pH of the affinity carrier. In addition, according to the second embodiment of the present invention, the purified monomeric antibody can be obtained at high content (high purity).

In the brief description of the drawings, the first embodiment refers to as FIGS. 1 to 10 and 12 to 16, and the second embodiment refers to as FIG. 1 to 16.

MODE FOR CARRYING OUT THE INVENTION

Figure 1:
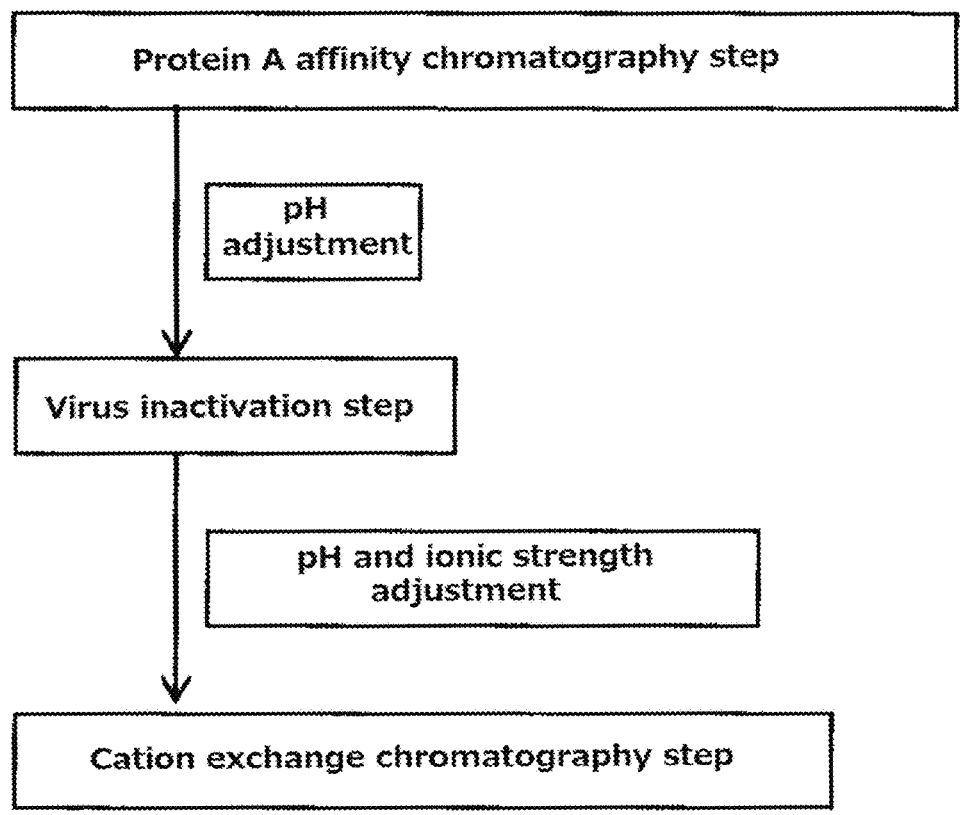
FIG. 1 is a conventional flow chart in which the protein A affinity chromatography step, the virus inactivation step, and the cation exchange chromatography step are conducted in this order.

In the first embodiment of the present invention, the novel method for purifying an antibody and the like (an antibody or a substance derived from an antibody) is featured in that a carrier 1 having an affinity ligand with affinity for the antibody and the like and a carrier 2 having a cation exchange group are used to prepare an integrated column 1 connecting a column containing the carrier 1 and a column containing the carrier 2 or a column 2 having a mixture of the carrier 1 and the carrier 2, the antibody and the like is applied to the column 1 or the column 2, and then the adsorbed antibody and the like is eluted from the column 1 or the column 2.

In the first embodiment of the present invention, the column 1 and the column 2 are also referred to as an integrated column and a mixed column, respectively, and the "applying" can also mean "loading" in some cases.

For example, the purification method of the first embodiment of the present invention is a method for purifying an antibody and the like with a carrier 1 having an affinity ligand with affinity for the antibody and the like and a carrier 2 having a cation exchange group, wherein a solution containing the antibody and the like is applied to an integrated column 1 connecting a column containing the carrier 1 and a column containing the carrier 2 in series or a column 2 having a mixture of the carrier 1 and the carrier 2, and an eluate is passed through the integrated column or the mixed column to elute the loaded antibody and the like.

In the first embodiment of the present invention, preferably, the carrier 1 having an affinity ligand does not contain a cation exchange group, and preferably, the carrier 2 having a cation exchange group does not contain an affinity ligand.

The second embodiment of the present invention is featured in that an antibody and the like is separated from a cation exchange carrier at acidic elution pH in which a target molecule (an antibody and the like) is eluted from an affinity carrier 1, or an affinity carrier 1 and a cation exchange carrier 2 are used to prepare an integrated column 1 connecting a column containing the affinity carrier 1 and a column containing the cation exchange carrier 2 or a column 2 having a mixture of the affinity carrier 1 and the cation exchange carrier 2, the antibody and the like is applied to the column 1 or the column 2, and then the adsorbed antibody and the like is eluted from the column 1 or the column 2. In the present invention, the column 1 and the column 2 are also called an integrated column and a mixed column, respectively, and the "applying" can also mean "loading". That is, in the second embodiment of the present invention, the method for using a carrier having a cation exchange group is featured in that a solution containing an antibody or a substance derived from an antibody is applied to a carrier having a cation exchange group having a carboxyl group-containing ligand and pKa of 4.0 or more, and the antibody or the substance derived from the antibody is eluted by an acidic buffer having pH of 4.0 or less. In the second embodiment of the present invention, the carrier 1 having an affinity ligand preferably does not contain a cation exchange group, and the carrier 2 having a cation exchange group preferably does not contain an affinity ligand. These features of the second embodiment may be used in the first embodiment, or may constitute the first embodiment.

Figure 2:
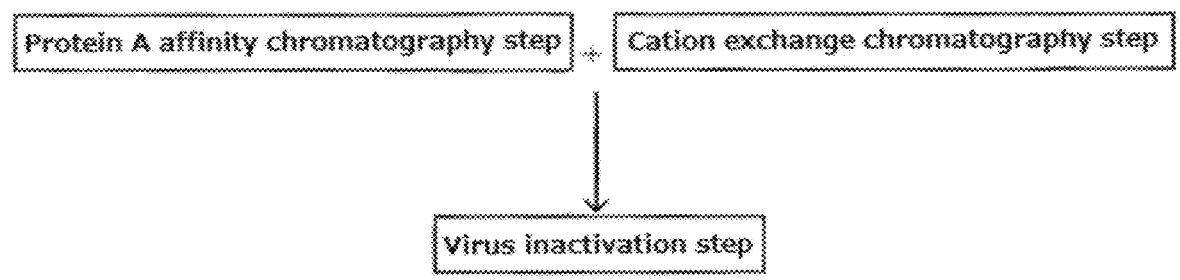
FIG. 2 is a flow chart showing one example of the present invention, in which the virus inactivation step is conducted after the protein A affinity chromatography step and the cation exchange chromatography step are conducted simultaneously.

The first embodiment and the second embodiment of the present invention can be performed by operating a column in which antibody affinity chromatography purification and cation exchange chromatography purification are integrated. That is, since two chromatography steps (see FIG. 1, conventional flow chart) can be performed in a single chromatography step (see FIG. 2, purification flow chart of the first embodiment and the second embodiment of the present invention), it is possible to reduce the number of steps, and to improve the production efficiency without using buffers required in respective steps. Also, it is possible to achieve a high content (high purity) of the monomeric antibody.

Hereinafter, the affinity carrier, the cation exchange carrier and the integration of the cation exchange carrier and the antibody affinity carrier into one chromatography in the first embodiment and the second embodiment of the present invention will be specifically described.

Carrier having affinity ligand (affinity carrier) The "carrier having an affinity ligand" (hereinafter, also called a carrier 1 having an affinity ligand, an affinity carrier or an affinity carrier 1 in some cases) in the first embodiment and the second embodiment of the present invention indicates a carrier in which a substance for selectively collecting (binding to) a target (objective) molecule from a certain group of molecules, on the basis of the specific intermolecular affinity represented by binding between an antigen and an antibody, is immobilized as a ligand to a water-insoluble carrier.

The affinity ligand which can be used in the first embodiment and the second embodiment of the present invention is not specifically limited, so long as the substance has a characteristic capable of specifically binding to an antibodies and the like as a target molecule. The affinity ligand is preferably a peptide ligand, a protein ligand, or a chemosynthetic ligand (synthesized compound). From the viewpoint of specificity to a target molecule, a peptide ligand or a protein ligand is further preferable. Among them, it is especially preferable that the affinity ligand with affinity for the antibodies is protein A, protein G, protein L, protein H, protein D, protein Arp, protein FcγR, a synthetic peptide ligand for binding an antibody and an analog substance thereof.

In the first embodiment and the second embodiment (especially, the first embodiment) of the present invention, the affinity ligand is more preferably protein A, protein G, protein L or an analog substance thereof, and most preferably protein A, or an analog substance thereof.

In the first embodiment and the second embodiment of the present invention, the affinity ligand is not specifically limited, so long as the substance has a target molecule-binding domain (a monomer peptide or protein, a single domain). It is preferable that the affinity ligand is a polymer peptide or a protein linked with preferably two or more domains (multiple domains), more preferably 2 to 10 domains, 2 to 8 domains, and further preferably 2 to 6 domains. The polymer protein may be a homopolymer such as a homodimer and a homotrimer which is a linked body of a single target molecule-binding domain. The polymer protein may be a heteropolymer such as a heterodimer and a heterotrimer which is a linked body of plural kinds of target molecule-binding domains so long as the target molecules are identical.

As a method for linking the target molecule-binding domains of the affinity ligand of the first embodiment and the second embodiment of the present invention, a method of not destabilizing a three-dimensional structure of the polymer protein is preferable. The method includes, but not limited to, for example, a method of linking the target molecule-binding domains via a terminal amino acid of the domain sequence, a method of linking the target molecule-binding domains not via an amino acid residue of the domain sequence, or a method of linking the target molecule-binding domains via amino acid residues other than one or plural domain sequences.

As the affinity ligand of the first embodiment and the second embodiment of the present invention, a fusion protein in which a polymer protein as one component is fused to another protein having a different function can be preferably used. Examples of the fusion protein may include, but not limited to, a protein to which albumin or GST (glutathione S-transferase) are fused, and a protein to which a nucleic acid such as a DNA aptamer, a drug such as an antibiotic, and a macromolecule such as PEG (polyethylene glycol) are fused.

In the first embodiment of the present invention, generally, 10% DBC of the affinity carrier 1 to IgG at 6 minutes of contact time is preferably 1 mg/mL or more and 100 mg/mL or less, more preferably 10 mg/mL or more, even preferably 15 mg/mL or more, even more preferably 20 mg/mL or more, and particularly preferably 30 mg/mL or more.

The 10% DBC can be determined, for example, by the following formula.

$$DBC_{10\%}=(V_{10\%}-V_d)C_o/V_c$$

(wherein $V_{10\%}$ represents a solution volume at the time of 10% break through of IgG, $V_d$ represents a piping volume (for example, including the piping volume from the injection to the column inlet, and the piping volume from the column outlet to the detector), $C_o$ represents an antibody concentration of the loading solution (mg/mL), and $V_c$ represents a column volume). In measuring the $DBC_{10\%}$, the measurement is preferably conducted at a predetermined flow rate, namely, with a predetermined contact time (for example, 1 to 10 minutes, preferably 3 to 6 minutes).

In the first embodiment and the second embodiment of the present invention, the affinity carrier has the volume average particle diameter of, for example, 1 μm or more and 1000 μm or less, preferably 5 μm or more and 500 μm or less, more preferably 10 μm or more and 200 μm or less, even preferably 150 μm or less, even more preferably 120 μm or less, and especially preferably 100 μm or less.

Carrier Having Cation Exchange Group (Cation Exchange Carrier)

The "carrier having a cation exchange group" (hereinafter, also referred to as a carrier 2 having a cation exchange group, a cation exchange carrier or a cation exchange carrier 2 in some cases) in the first embodiment and the second embodiment of the present invention may be those in which a cation exchange group is immobilized on the water-insoluble carrier such that the cation exchange group can function as a cation exchange group under conditions for eluting (desorbing) an antibody and the like of a target molecule from the affinity ligand, to capture the target molecule, and can elute (desorb) a monomer and an aggregate of the target molecule in this order depending on the ionic strength by counter ions such as sodium ions and potassium ions.

In order to collect the target molecule with a recovery of 80% or more at an acidic pH region for eluting the target molecule from the affinity ligand, it is preferred to use, as a cation exchange group, a cation exchange group having as a ligand a carboxyl group of a weak acidic group (carboxyl group-containing ligand). The carboxyl group-containing ligand can be derived from an acidic amino acid, and is more preferably derived from glutamic acid. Since an acidic pH of pH 4.0 or less is usually used for elution from the affinity carrier, the carboxyl group-containing ligand of a cation exchange ligand of the first embodiment and the second embodiment of the present invention has pKa of 4.0 or more in order to obtain high recovery at the pH. The carboxyl group-containing ligand has pKa of preferably 4.05 or more and 6.5 or less, more preferably 4.10 or more and 6.45 or less. If the pKa is low, the antibody recovery is decreased in some cases.

In preferred embodiment of the first embodiment of the present invention, it is recommended that the cation exchange group is a carboxyl group, a sulfone group or the like. Among these, a carboxyl group is preferred, and a carboxyl group having pKa of 4.0 or more is more preferred. Also, the carboxyl group can be derived from an acidic amino acid, and more preferably from glutamic acid. Further, in the elution pH region of the target molecule from the affinity ligand, it is preferred to avoid a local harsh acidic environment, and a weak acidic group is preferred. For example, when a carrier having protein A as an affinity ligand is used, it is preferred to use, as cation exchange group, a cation exchange group having a carboxyl group as a ligand.

In the first embodiment of the present invention, the cation exchange group has preferably pKa of 3.5 or more and 6.5 or less, more preferably 4.0 or more and 6.0 or less, and even preferably 4.1 or more and 5.5 or less. In the case of lower pKa, the recovery of the antibodies is decreased in some cases.

In the first embodiment and the second embodiment of the present invention, when a carrier having a cation exchange group, and an affinity carrier are used in an integrated column or in a mixed column, pKa of the cation exchange group and elution pH preferably satisfy the relationship: pKa of cation exchange group≥pH of elution, and more preferably satisfy the relationship: pKa of cation exchange group>pH of elution.

A suitable condition for using both the carrier having a cation exchange group and the affinity carrier was found in the present invention, while a carrier having a cation exchange group was conventionally used alone under the condition: pKa of cation exchange group<pH of elution.

As long as the aforementioned relationship is satisfied, the target protein (antibody and the like) is largely charged positively at the time of elution, and the conversion of the ligand of the cation exchange group from the negative side to the positive side is relatively suppressed, so that further positively charged aggregates of the antibody and the like can be collected to purify the monomeric antibody more easily.

In the first embodiment and the second embodiment of the present invention, the cation exchange carrier has the volume average particle diameter of, for example, 1 μm or more and 1000 μm or less, preferably 5 μm or more and 500 μm or less, more preferably 10 μm or more and 200 μm or less, even preferably 150 μm or less, even more preferably 120 μm or less, and especially preferably 100 μm or less.

In the first embodiment and the second embodiment of the present invention, the cation exchange carrier has preferably the ion exchange capacity of 0.001 mmol/mL or more and 0.5 mmol/mL or less.

In the first embodiment and the second embodiment of the present invention, 10% DBC of the carrier having a cation exchange group having a carboxyl group-containing ligand (the cation exchange carrier 2) to IgG at 6 minutes of contact time is preferably 1 mg/mL or more and 200 mg/mL or less, more preferably 10 mg/mL or more, even preferably 15 mg/mL or more, even more preferably 20 mg/mL or more, and particularly preferably 30 mg/mL or more. The 10% DBC can be determined, for example, by the following formula.

$$DBC_{10\%}=(V_{10\%}-V_d)C_o/V_c$$

(wherein, $V_{10\%}$ represents a solution volume at the time of 10% break through of IgG, $V_d$ represents a piping volume (for example, including the piping volume from the injection to the column inlet, and the piping volume from the column outlet to the detector), $C_o$ represents an antibody concentration of the loading solution (mg/mL), $V_c$ represents a column volume). Preferably, $DBC_{10\%}$ is measured at a predetermined flow rate, namely, with a predetermined contact time (for example, 1 to 10 minutes, preferably 3 to 6 minutes), at a predetermined pH (for example, 3 to 5, particularly 4).

Water Insoluble Carrier (Carrier)

A "water-insoluble carrier" used in the first embodiment and the second embodiment of the present invention is a carrier made of water-insoluble base material, and is not particularly limited so long as the antibody affinity ligand and the cation exchange group are immobilized on the carrier. The water-insoluble carrier includes inorganic carriers such as glass beads and silica gel; organic carriers such as synthetic polymers including cross-linked polyvinyl alcohol, cross-linked polyacrylate, cross-linked polyacrylamide, cross-linked polystyrene and polysaccharides including crystalline cellulose, cross-linked cellulose, cross-linked agarose, cross-linked dextran; and composite carriers of combinations of these carriers such as organic-organic composite carrier and organic-inorganic composite carrier. Examples of commercial products thereof can include GCL 2000 (porous cellulose gel), Sephacryl S-1000 (covalently cross-linked copolymer of allyl dextran and methylene bis acrylamide), Toyopearl (acrylate carrier), Sepharose CL4B or Rapid Run Agarose Beads (cross-linked agarose carrier), Cellufine (cross-linked cellulose carrier) and the like.

In addition, the water-insoluble carrier used in the first embodiment and the second embodiment of the present invention has desirably a large surface area and is preferably a porous matrix having a large number of fine pores with a suitable size, from the viewpoint of productivity to be treated per unit time. The carrier may be any form such as bead, monolith, fiber, or membrane (including hollow fiber), and the carrier can be selected from any form of these. The water-insoluble carrier is preferably a porous bead because the separation matrix can effectively function by concertedly working the affinity ligand and the cation exchange group arranged on the water-insoluble carrier, causing proximity of physical distance between the affinity ligand and the cation exchange group, and obtaining a given contact time. When the cation exchange group is immobilized on the carrier to which the affinity ligand is fixed, a carrier made of polysaccharides or modified with monosaccharides or polysaccharides is preferable from the viewpoint of easy of introduction of the affinity ligand. Concretely, the carrier is not particularly limited, and is preferably an agarose carrier and a cellulose carrier.

In the first embodiment of the present invention, as a method for immobilizing the affinity ligand to the water-insoluble carrier or the separation matrix, a general method can be used. For example, an amino group of the affinity ligand may bind to a carrier via a formyl group introduced on the carrier, and an amino group of the affinity ligand may bind to a carrier via an activated carboxyl group on the carrier. In addition, these water-insoluble carriers are activated so that the ligand can covalently bind to the carrier before introduction of the affinity ligand. A commercially available activated carrier may be used, and activation may be carried out by an operator himself/herself.

In the first embodiment of the present invention, a functional group introduced to the water-insoluble carrier by activation is not specifically limited, so long as the functional group can form a covalent bond with the affinity ligand. Examples of the functional group may include a reactive functional group ("activating group") such as an epoxy group (epichlorohydrin), a hydroxy group activated by cyanogen bromide, N,N-disuccinimidyl carbonate (DSC) and the like, an aldehyde group or an activated carboxylic acid group (for example, N-hydroxysuccinimide (NHS) ester, carbonyldiimidazole (CDI) activated ester), and the like (Hermanson G. T. et al, "Immobilized Affinity Ligand Techniques, Academic Press", 1992, U.S. Pat. Nos. 5,874,165, 3,932,557, 4,772,653, 4,210,723, 5,250,613, EP 13 52957, WO 2004/074471). These functional groups include a functional group in which the affinity ligand directly, covalently binds to the carrier, and a functional group in which a linear, branched, or cyclic linker or spacer is used.

In the first embodiment of the present invention, as a method for immobilizing a protein ligand among the affinity ligands to the carrier, a method for reacting a part of the functional group of the protein with a part of the functional group of the carrier can be used. Examples of the major functional group in the protein which can be utilized for the reaction (activating group) may include, but not limited to, N-terminal amino acid and an amino group of a lysine (Lys) side chain, or a thiol group of a cysteine (Cys) side chain, or C-terminal amino acid and carboxyl groups of a glutamic acid (Glu) side chain and an aspartic acid (Asp) side chain.

In addition, in the first embodiment of the present invention, as a method for immobilizing the proteinous antibody affinity ligand to the water-insoluble carrier by controlling the orientation of the ligand, a method of utilizing protein A having cysteine at the C-terminus is proposed (U.S. Pat. No. 6,399,750, Ljungquist C. et al., "Eur. J. Biochem." 1989, Vol. 186, p. 557-561).

Examples of immobilization techniques utilizing a linker may include not only a method of ensuring the distance between the carrier and the ligand to exclude the steric hindrance aiming at provision of high performance, but also a method of giving and forming a functional group (for example, a charged amine) in a linker or a spacer. Improvement of separation performance by improvement of immobilization yield by effectively accumulating the ligand in the portion of a linker or a spacer at the time of immobilization of the antibody affinity ligand has been examined. For example, the immobilization technique includes an immobilization technique of a protein ligand to an agarose carrier derivatized by an NHS-activated carboxylic acid as a part of a linker arm (U.S. Pat. No. 5,260,373, JP2010-133733, JP2010-133734).

In addition, a method for separately immobilizing an antibody affinity ligand on a water-insoluble carrier by utilizing an associative group on the carrier besides a linker or a spacer in which the antibody affinity ligand is accumulated on a carrier without forming a covalent bond between the associative group and the antibody affinity ligand is also proposed (JP2011-256176).

In the first embodiment and the second embodiment of the present invention, as a technique to immobilize or introduce a cation exchange group to a water-insoluble carrier, a technique used for production of a cation exchanger can be usually utilized. For example, a technique to introduce a carboxymethyl group to a sugar skeleton includes, but not limited to, a method of making monochloroacetic acid react under alkaline conditions, and a method of introducing a sulfate group includes, but not limited to, a method of making sulfuric acid react under alkaline conditions.

It is also possible to introduce a carboxyl group by introducing an active group which reacts with an amino group on a water-insoluble carrier, and immobilizing an amino acid via an amino group of the amino acid.

For example, a cation exchange group can be introduced from covalent binding due to reductive amination of the aldehyde group and the amino group on the carrier, by activating the carrier from reaction of sodium periodate with a diol group present in or introduced to the water-insoluble carrier to introduce an aldehyde group, and adding a molecule having an amino group and a cation exchange group in a single molecule, and carrying out reduction treatment after formation of an imine. The cation exchange group may be directly immobilized to the water-insoluble carrier, and may be indirectly immobilized via a spacer, linker and the like.

In addition, so long as the cation exchange group can function as a cation exchanger under acidic pH conditions that a target molecule is eluted (released) from the affinity ligand, the cation exchange group, the spacer or the linker may include a functional group having other functions, and the molecular shape thereof is also not particularly limited. A method for introducing a carboxyl group of an amino acid is preferable as a method of preparing a material of a separation matrix for antibody purification, from the viewpoint of toxicity in a case where the ligand is leached.

The first embodiment and the second embodiment of the present invention are featured in that an antibody and the like is separated from a cation exchange carrier at acidic elution pH in which a target molecule is eluted from an affinity carrier, or an affinity carrier and a cation exchange carrier are used to prepare an integrated column 1 connecting a column containing the affinity carrier and a column containing the cation exchange carrier or a column 2 having a mixture of the affinity carrier and the cation exchange carrier, the antibody and the like is applied to the column 1 or the column 2, and then the adsorbed antibody or the like is eluted from the column 1 or the column 2. As representative examples of the first chromatography and the second chromatography used in the purification platform process of antibody drugs, for example, a combination of protein A chromatography and cation chromatography is used.

In the first embodiment and the second embodiment of the present invention, the ability of separating a monomeric substance and an aggregate by protein A chromatography used in the first chromatography is low, and robustness of the separation is also poor. Thus, in general, elution conditions that high recovery rate can be obtained by minimizing degeneration and aggregation of an antibody or an Fc-containing molecule as a target molecule are selected, and removal of the impurity such as the aggregate and the like is carried out in the subsequent processes.

In the first embodiment and the second embodiment of the present invention, as the second chromatography, when cation exchange chromatography is selected, the aggregate and other contaminants are generally removed by adsorption and desorption mode. However, in this chromatography, the pH and ionic strength of the eluate from the carrier having protein A ligand (the protein A carrier) is required to adjust to pH and ionic strength appropriate for adsorption of cation exchange chromatography. Thus, the conditions of the cation exchange chromatography step are necessarily also set after setting conditions of protein A chromatography step. In addition, while there are a wide variety of controlling factors, efficient separation of the impurity such as the aggregate is not necessarily possible.

On the other hand, when the methods of the first embodiment and the second embodiment of the present invention are used, the two-step chromatography operation can be reduced to the one-step operation, and reduction in the number of types and the use amount of the employed buffers, and further reduction in the operation time can be expected by preparing the integrated column or the mixed column including the affinity carrier and the cation exchange carrier, and adsorbing the antibody and the like on the integrated column or the mixed column, and eluting the antibody and the like from the integrated column or the mixed column.

In addition, the novel method for purifying an antibody of the first embodiment and the second embodiment of the present invention can obtain a fraction of an eluate of containing high content of the monomeric substance by setting the ionic strength and the like at a narrow pH range for eluting the target molecule from the affinity ligand. Especially in purification of a monoclonal antibody, since the elution pH is significantly separated from the isoelectric point of the target molecule, there is no significant difference in the range of the elution ionic strength of each antibody. Thus, it is possible to set conditions of various target molecules in a narrow range. Furthermore, when modified protein A ligand is used as the affinity ligand, the elution pH range can be set to be further narrower range, and effective washing is also possible due to use of alkaline CIP (cleaning in place; stationary washing). Thus, utilization of modified protein A is preferable from the viewpoint of construction of a robust process.

In the first embodiment and the second embodiment of the present invention, when other chromatography carrier is used in the integrated column or the mixed column without using the affinity carrier, in other words, when the ionic exchange carrier and the hydrophobic chromatography carrier are used in the integrated column or the mixed column, setting of conditions for each target molecule is different depending on differences in hydrophobicity and isoelectric point and the like, and the combination of the ionic exchange carrier and the hydrophobic chromatography carrier results in low specificity, even if the target molecule is a monoclonal antibody. Thus, it is difficult to make a platform as a recovery step.

In the first embodiment and the second embodiment of the present invention, the integrated column or the mixed column including the affinity carrier and the cation exchange carrier can not only exhibit high specificity with the affinity ligand at the time of adsorption, but also easily set conditions thereof by setting ionic strength in the range of the elution conditions of the affinity ligand. Thus, the integrated column or the mixed column are more excellent than the combination of other carrier without using the affinity carrier 1.

There disclosed a technique for eliminating a holding tank between protein A chromatography and cation exchange chromatography by completely capturing on the cation exchange chromatography column the whole amount of the antibody that has temporarily been adsorbed on the protein A chromatography column and eluted from the protein A chromatography column, and then eluting the antibody with a buffer at pH of 5.0 to 9.0. However, the technique is distinguished from the second embodiment of the present invention in that as the elution pH from the cation exchange carrier, higher pH than the elution pH from the affinity carrier is used. Also, the first embodiment and the second embodiment of the present invention are essentially different from the prior art such as WO2011/017514 in that the affinity carrier and the cation exchange carrier can be used in an integrated column or a mixed column in an integrated manner, a target substance can be fractionated in the course of elution in a single operation, the elution pH is less than 5.0 or 4.0 or less, and elution of the cation exchange carrier is conducted at the same pH as the elution pH of the affinity carrier.

More concretely, as to the method for using the integrated column or the mixed column including the affinity carrier and the cation exchange carrier in the first embodiment and the second embodiment of the present invention, when a target molecule such as an antibody is adsorbed around neutral pH, it is preferable to add a counter ion of the cation exchange group at a certain concentration or higher. Thus, the cation exchange group does not work under the conditions. In addition, if the cation exchange group works, a nonspecific adsorbate derived from the cation exchange group can be washed and removed with a solution having further higher ionic strength. On the other hand, the ionic strength does not inhibit adsorption of the affinity ligand, and enables adsorption of an objective substance with high specificity. Additionally, a molecule which nonspecifically adsorbs to the base material, the linker, the spacer, the ligand and the target molecule can be effectively washed and removed by use of a washing fluid having high ionic strength.

The present invention can show high specificity for a recombinant monoclonal antibody which is expressed in a culture supernatant because in general, it contains an ionic strength close to that of a body fluid of a human and the like, even if directly subjected to the integrated column or the mixed column of the present invention. Additionally, a contaminant can be further reduced by a washing fluid having a higher ionic strength. It is preferable to elute the target molecule from the cation exchange group in a manner dependent on ionic strength by the linkage with the elution of the target molecule from the affinity carrier at lower pH, after the passage of the buffer having lower ionic strength so as to exert the function of the cation exchange group and before eluting a composition containing the target molecule from the affinity carrier.

When a column A packed with an affinity carrier and a column B packed with a cation exchange carrier are connected in the first embodiment and the second embodiment of the present invention, it is suited to directly connect the column B to the column A such that the column A is upstream, and it is preferred that the connecting part is formed of a straight pipe without provision of a branch valve on the way. However, a branch valve may be inserted on the way as long as they are directly connected as a flow channel.

In the first embodiment and the second embodiment of the present invention, the function of the integrated columns or the mixed column including the affinity carrier and the cation exchange carrier can be adjusted by the ratio between the affinity carrier and the cation exchange carrier. When the binding capacity of the target substance under the neutral condition of the affinity carrier is larger than the binding capacity of the cation exchange carrier at acidic elution pH from the affinity carrier, the target substance tends to be eluted from the column even at a low ionic strength at the time of acidic elution. When the binding capacity of the affinity carrier is similar to or lower than the binding capacity of the cation exchange carrier, the antibody eluted from the affinity carrier completely migrates to the cation exchange carrier at a low ionic strength. Thus, it is necessary to set the higher ionic strength at the elution in the view of obtaining higher recovery. In any case, it is possible to control the recovery and the monomer ratio by adjusting the ionic strength and/or pH.

In the first embodiment and the second embodiment of the present invention, the ratio between the binding capacity of the affinity carrier (for example, 10% DBC) and the binding capacity of the cation exchange carrier (for example, 10% DBC) is not particularly limited. The ratio of the binding capacity of the cation exchange carrier to IgG at 6 minutes of contact time relative to the binding capacity of the affinity carrier to IgG at 6 minutes of contact time under each adsorption condition is preferably 10 times or less, and more preferably 5 times or less. Also the lower limit is preferably 1/10 time or more, and more preferably 1/5 time or more.

For example, the ratio of the binding capacity may be a ratio obtained from 10% DBC values of the affinity carrier and the cation exchange carrier.

In the first embodiment and the second embodiment of the present invention, the ratio of the affinity carrier to the cation exchange carrier that constitute the integrated column or the mixed column (affinity carrier/cation exchange carrier) is preferably 1/20 or more and 20/1 or less, more preferably 1/5 or more and 5/1 or less on the basis of the volume.

In the first embodiment and the second embodiment of the present invention, the target molecule to be purified by the integrated column or the mixed column including the affinity carrier and the cation exchange carrier is an antibody and the like (immunoglobulin G and an analog thereof). Also, the target molecule includes molecules that are generally called antibodies, Fc fusion proteins (Fc-containing molecules) in which an Fc region of a constant region of an immnunoglobulin molecule, and other functional protein or peptide are fused, and low molecular antibodies. These are utilized as raw materials for antibody drugs. Specific examples of the antibody and the like preferably include immunoglobulin G, immunoglobulin G derivatives, Fc-containing molecules, and low molecular antibodies such as Fab, scFv, and diabody.

Hereinafter, in the first embodiment and the second embodiment of the present invention, the method for using the integrated column or the mixed column including the affinity carrier and the cation exchange carrier to adsorb and elute the antibody and the like will be described in detail by exemplifying the case where the target molecule is immunoglobulin G. However, the first embodiment and the second embodiment of the present invention are not limited thereto.

In the first embodiment and the second embodiment of the present invention, preferred methods for using the integrated column or the mixed column include (1) a method in which a column packed with an affinity carrier is connected to a column packed with a cation exchange carrier such that the column packed with the cation exchange carrier is downstream to prepare an integrated column, a solution containing an antibody and the like is applied to the integrated column under condition of neutral pH (for example, pH 6 or more and 9 or less), and the antibody and the like is eluted by an acidic buffer having pH of 4.0 or less, and (2) a method in which an affinity carrier is mixed with a cation exchange carrier to prepare a mixed column, a solution containing an antibody and the like is applied to the mixed column under condition of neutral pH, and the antibody and the like is eluted by an acidic buffer having pH of 4.0 or less.

In the first embodiment and the second embodiment of the present invention, purification of a target molecule (antibody) using the integrated column or the mixed column including the affinity carrier and the cation exchange carrier is roughly composed of 4 steps: an adsorption step, a washing step, a step of adjusting the ionic strength, and an elution step. In addition, purification may comprise a step for reuse such as subsequent regeneration step and/or CIP step, and re-equilibration step.

In the first embodiment and the second embodiment of the present invention, a common affinity column chromatography purification method can be used in the adsorption step. That is, in one example, after adjusting pH of a protein solution containing an antibody and the like (for example, immunoglobulin G) to approximately neutrality, the resulting solution is applied to the integrated columns or the mixed column including the affinity carrier and the cation exchange group (cation exchange carrier) of the first embodiment and the second embodiment of the present invention, and the antibody and the like (for example, immunoglobulin G) is specifically adsorbed to the column packed with the affinity carrier or to the affinity carrier. For example, when a protein A carrier is used in the affinity carrier, the loading pH thereof is preferably 6 or more, more preferably 6.3 or more and 9 or less, and even preferably 6.5 or more and 8.5 or less. In purification of immunoglobulin G produced by mammalian cultured cells, special adjustment of the ionic strength is not required, and nonspecific adsorption can be suppressed by preliminarily elevating the ionic strength. In the adsorption step, a solution containing an antibody or a substance derived from an antibody at a predetermined concentration is applied to the carrier, and as a solvent for the solution containing an antibody or a substance derived from an antibody, for example, PBS (approximately 10 mM phosphoric acid, approximately 150 mM NaCl etc.) may be used. Also an equilibration step may be conducted prior to the adsorption step, and as a solvent for the equilibration buffer, for example, PBS (approximately 10 mM phosphoric acid, approximately 150 mM NaCl etc.) may be used.

In the washing step of the first embodiment and the second embodiment of the present invention, an appropriate amount of a buffer within the range of the conditions under which the affinity ligand functions is passed through the column, to wash the column. That is to say, the preferable range of pH may be the same range as that of the above-mentioned case of the adsorption step (near neutral pH). For example, pH is preferably 6 or more. At this point, the antibody and the like (for example, immunoglobulin G) of the target molecule is adsorbed to the affinity carrier. At this time, impurities such as host cell proteins can be effectively removed in some cases, by optimization of the ionic strength and the composition at near neutral pH. At the time of the loading and washing, conditions under which the cation exchange group does not function is preferable. That is to say, it is preferable that a washing buffer having pH near neutral and a certain level or more of ionic strength is utilized, and impurities nonspecifically remaining in the separation matrix and/or in the column via immunoglobulin G can be washed in this process.

In the first embodiment and the second embodiment of the present invention, a washing step is conducted before starting the elution described below after applying a solution containing an antibody and the like. The number of the washing step is, for example, at least one time, and preferably two or more times. A preferred example of the washing step includes, for example, the following non-limiting examples:

(1) an example in which the integrated column or the mixed column is equilibrated with an equilibration buffer (equilibration solution), the solution containing an antibody or a substance derived from an antibody is applied to the integrated column or the mixed column, and the integrated column or the mixed column is washed with a washing buffer 2 (second washing solution) having higher pH than that of the eluate and lower ionic strength than those of the equilibration buffer and the solution containing an antibody or a substance derived from an antibody before the elution, (2) an example in which the integrated column or the mixed column is equilibrated with an equilibration buffer, the solution containing an antibody or a substance derived from an antibody is applied to the integrated column or the mixed column, the integrated column or the mixed column is washed with a washing buffer 1 (first washing solution) having higher pH than that of the eluate and ionic strength greater than or equal to those of the equilibration buffer and the solution containing the antibody or the substance derived from the antibody, and is washed with a washing buffer 2 (second washing solution) having higher pH than that of the eluate and lower ionic strength than those of the equilibration buffer and the solution containing the antibody or the substance derived from the antibody before elution.

In the above examples of (1) and (2), a washing method used in common protein A chromatography is applied to an integrated column or a mixed column, thus being able to wash out not only the impurities that are non-specifically adsorbed to the protein A carrier but also the impurities adsorbed to the cation exchange carrier. The above (1) is preferably conducted, for example, on an antibody having high purification purity, and the above (2) is preferably conducted, for example, on a culture supernatant. The second washing solution used in the above (1) and (2) is, for example, a solution of 10 mM Tris/HCl pH 7, and the first washing solution used in the above (2) is, for example, a solution of 10 mM Tris 1 M NaCl pH 7. Prior to the above (1) and (2), prewashing may be conducted with a solution (for example, PBS) having the same ionic strength and pH as those of the equilibration solution.

In the ionic strength adjustment step of the first embodiment and the second embodiment of the present invention, an approximately neutral buffer having low ionic strength is passed through the column to be ready for expression of the ionic strength-dependent elution function by the cation exchange carrier at the time of elution. More preferably, the ionic strength is lower than the ionic strength of the eluate.

In the elution step of the first embodiment and the second embodiment of the present invention, the cation exchange separation mode functions at the time of the elution of the target substance from the affinity carrier to collect a fraction containing high content of the monomeric antibody as a fraction eluted at lower ionic strength, by using the combination of acidic pH and the ionic strength.

The elution pH of the antibody and the like (for example, imunoglobulin G) from the affinity carrier can be applied to pH of the eluate. The pH is mainly determined according to the separation condition selected from the kinds of the affinity carrier and the antibody and the like (for example, immunoglobulin G), and the setting of the particular conditions is not required. The pH of the eluate is preferably higher pH in the range capable of eluting the antibody and the like from affinity carrier in the view of controlling the production of the aggregates and the like. In the first embodiment and the second embodiment of the present invention, the elution pH of the antibody and the like is 4.0 or less, preferably 3.95 or less, more preferably 3.9 or less, and even preferably 3.8 or less. The elution pH is, for example, 3.0 or more, preferably 3.2 or more, and more preferably 3.5 or more.

In other embodiment of the first embodiment, the elution pH of the antibody and the like is preferably less than 5.0, more preferably 4.5 or less, and even preferably 4.0 or less. The elution pH is, for example, 3.0 or more, preferably 3.2 or more, and more preferably 3.5 or more.

In the first embodiment and the second embodiment of the present invention, when the affinity carrier is protein A carrier, for example, pH of the eluate is set to 2 or more and less than 5.0, or 2 or more and 4.0 or less. From the view of avoiding acid modification of the target molecule, pH of the eluate is preferably 3.0 or more, and particularly preferably 3.5 or more. It is preferable that the upper limit of the eluate pH is the same as those mentioned above.

When an alkali-resistant type of a modified protein A ligand is used in the first embodiment and the second embodiment, the elution pH thereof is generally mainly set within the range of 3.5 to 4.0, but not limited thereto. In addition, the ionic strength for the elution not only depends on the introduction ratio of the affinity carrier and the cation exchange carrier, but also depends on the load amount of the antibody and the like (for example, immunoglobulin G) per unit volume. However, the optimized conditions can be easily set by a gradient elution experiment or a stepwise elution experiment.

In the elution condition of the cation exchange carrier of the second embodiment or the elution condition of the first embodiment, either gradient elution or stepwise elution with salt concentration is applicable. From the viewpoint of the simplification of the operation, the condition setting capable of collecting the antibody by stepwise elution at high content of the monomeric antibody is preferable, and gradient elution is preferable due to the ease of condition setting.

In the first embodiment and the second embodiment, the antibody and the like may be eluted by the eluate having an acidic pH with an ionic strength linear gradient, or the antibody and the like may be eluted by the eluate having an acidic pH with an ionic strength step gradient.

Moreover, when impurity including an aggregate remains in the column and is not mixed in the elution fraction even with the combination of the ionic strength and acidic elution pH of the washing step, the step of adjusting the ionic strength can be omitted.

In the first embodiment and the second embodiment of the present invention, at the start of the elution, it is preferred that the pH of the eluate is kept constant, and the ionic strength of the eluate is increased continuously or stepwise. The eluate may be those commonly used, and includes, for example, acetic acid and citric acid. The pH of the eluate is preferably 3 or more and 4.0 or less, more preferably 3.1 or more and 3.95 or less, and even preferably 3.2 or more and 3.90 or less. In the first embodiment, in particular, the pH of the eluate is preferably 3 or more and 5 or less, more preferably 3.1 or more and 4.5 or less, and even preferably 3.2 or more and 4.0 or less. In the first embodiment and the second embodiment, the ionic strength is increased continuously or stepwise preferably within the range of 0.1 mM or more and 2000 mM or less, more preferably within the range of 0.5 mM or more and 1000 mM or less, and further preferably within the range of 1 mM or more and 500 mM or less.

In the first embodiment and the second embodiment of the present invention, the antibody and the like (for example, imunoglobulin G) purified by the integrated column or the mixed column including the affinity carrier and the cation exchange carrier is eluted with higher monomer selectivity than that of an antibody affinity separation matrix based on a single separation mode, and has high monomer content in the eluate thereof.

Also when the affinity carrier based on the single separation mode is used, it is possible to increase the monomer content to some degree by optimizing the elution pH, the ionic strength and the like. However, its effect is low, and expression of the effect is accompanied by greater decrease in recovery. By using the integrated column or the mixed column including the affinity carrier and the cation exchange carrier of the first embodiment and the second embodiment of the present invention, it is possible to efficiently achieve highly specific affinity purification and improvement in the monomer content mainly achievable by the cation exchange chromatography at a single chromatography operation, so that it becomes possible to reduce the load to the subsequent process, and to contribute to improvement in recovery of the whole process and improvement in the monomer content. That is, the novel method purifying an antibody in which the integrated column or the mixed column including the affinity carrier and the cation exchange carrier of the first embodiment and the second embodiment of the present invention can contribute to improvement in productivity of the production process and improvement in purity of antibody drugs.

The present application claims the benefit of priority to Japanese Patent Application Number 2013-192378 filed on Sep. 17, 2013 and Japanese Patent Application Number 2013-192379 filed on Sep. 17, 2013. The entire contents of the specification of Japanese Patent Application Number 2013-192378 filed on Sep. 17, 2013 and Japanese Patent Application Number 2013-192379 filed on Sep. 17, 2013 are hereby incorporated by reference.

EXAMPLES

The first embodiment and the second embodiment of the present invention will be explained more in detail on the basis of the Examples herein below, but the first embodiment and the second embodiment of the present invention is not limited to these Examples.

Preparation Example of Cation Exchange Carrier

Preparation of Carrier Introduced with Carboxyl Group

Preparation Example 1

As 4% agarose beads, 4 mL in wet volume of LOW Density GLYOXAL 4 Rapid Run (Agarose Bead Technologies) substituted with cold water were taken into a reaction vessel, and were washed 5 times with cold 1 M glutamic acid (pH 6). After recovery, the amount of the slurry was made up for 7 mL. The resulting slurry was overturned and stirred in a chromatochamber for 2 hours, and 0.5 mL of an aqueous 1 M dimethylamine borane solution was additionally put thereto, the mixture was stirred in a chromatochamber for 1.5 hours. Further, the mixture was overturned and stirred at room temperature overnight. The carrier was precipitated by centrifugation and thereafter the supernatant was removed so that the liquid amount became 6 mL. Twenty milligrams of sodium borohydride was directly added thereto, and the mixture was further overturned and stirred at room temperature for 2 hours. The mixture was sufficiently washed with water, 0.1 M citric acid, 0.1 M sodium hydroxide and PBS containing 0.5 M NaCl, to give an agarose carrier in which a carboxyl group was introduced to an aldehyde group by reductive amination via an amino group of glutamic acid. This cation exchange carrier is referred to as Glyoxal-COOH.

(Measurement of pKa and Ion Exchange Capacity of Cation Exchange Carrier (Carboxyl Group-Containing Ligand))

As a cation exchange carrier introduced with a carboxyl group, CM-Sepharose Fast Flow (GE Healthcare; cation exchange carrier A), TOYOPEARL CM-650 M (Tosoh Corporation; cation exchange carrier B), FRACTOGEL COO (M) (Merck Millipore Corporation; cation exchange carrier C), or Glyoxal-COOH (Preparation Example 1; cation exchange carrier D) was replaced with 1 M KCl (pH2) and titrated with 0.1 M NaOH to determine the pKa and ion exchange capacity. The result is shown in Table 1.

TABLE 1

|  | pKa | Ion exchange capacity (mmol/mL) |
|---|---|---|
| Cation exchange carrier A CM-Sepharose Fast Flow | 3.90 | 0.10 |
| Cation exchange carrier B TOYOPEARL CM-650M | 4.45 | 0.10 |
| Cation exchange carrier C Fractogel COO(M) | 5.08 | 0.09 |
| Cation exchange carrier D Glyoxal-COOH | 4.14 | 0.02 |

(Measurement of Binding Capacity of Cation Exchange Carrier at Acidic pH)

A column available from Omnifit (ID 0.66 cm×Height 7 cm) was packed with CM-Sepharose Fast Flow (GE Healthcare), TOYOPEARL CM-650 M (Tosoh Corporation), Fractogel COO (M) (Merck Millipore Corporation), or Glyoxal-COOH (Preparation Example 1) as a cation exchange carrier introduced with a carboxyl group, and binding capacity was measured in the following chromatography condition using a human polyclonal antibody (gamma globulin NICHIYAKU: NIHON PHARMACEUTICAL CO., LTD.) prepared into 0.5 mg/mL as a loading solution. The pH of the loading solution is set at 3.7, 4.2, or 4.7, binding capacity in each case was measured as a kinetic binding capacity of 10% break-through of IgG (10% DBC).

Chromatography Condition Used for Determination of 10% DBC Based on Cation Exchange Carrier
Column: ID 0.66 cm×Height 7 cm, 2.4 mL volume (manufactured by Omnifit Ltd.)
Flow rate: 0.4 mL/min (contact time: 6 minutes)
Polyclonal antibody (IgG): gamma globulin NICHIYAKU (NIHON PHARMACEUTICAL CO., LTD.)
Loading solution: 0.5 mg-IgG/mL (5 mM citric acid: pH 3.7, 4.2, or 4.7)
Equilibration solution: 5 mM citric acid (pH 3.7, 4.2, or 4.7)
Eluate: 50 mM citric acid, 0.5 M sodium chloride (pH 3.7)
CIP solution: 0.1 M sodium hydroxide, 1 M sodium chloride
Neutralizing and re-equilibrating solution: 5 mM citric acid (pH 3.7, 4.2, or 4.7)

Figure 3:
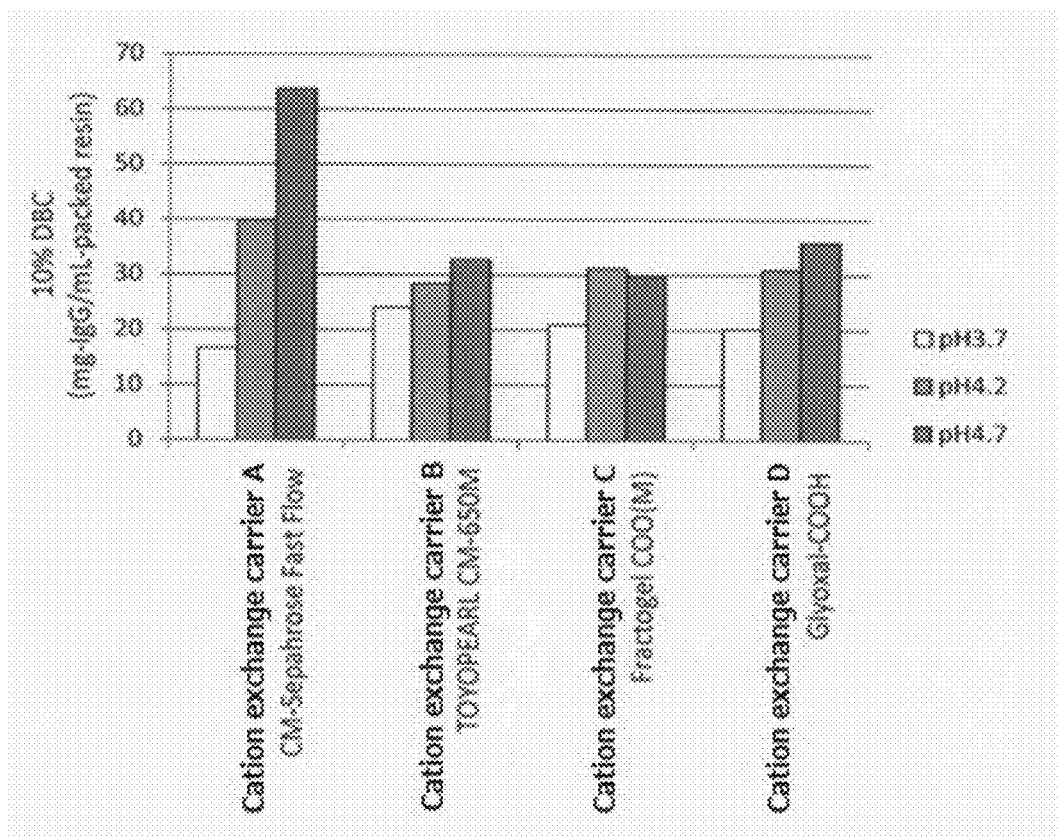
FIG. 3 is a chart showing dynamic binding capacity at 10% break through (10% DBC) of a carrier having each cation exchange group at pH 3.7, pH 4.2, or pH 4.7.
Figure 4:
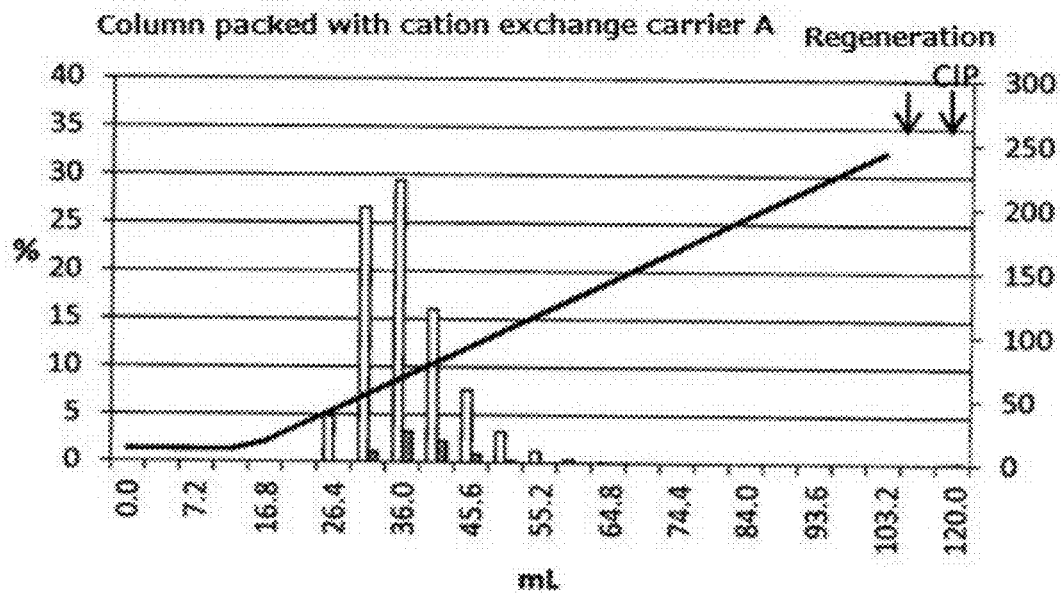
FIG. 4 is a chart showing elution of a monomeric antibody (outline column) and an aggregate of an antibody (hatched column) when a column packed with a carrier having a cation exchange group (cation exchange carrier A) is used. The horizontal axis represents an elution volume (mL), the left vertical axis represents a peak area rate (%), and the right vertical axis represents an ionic strength (mM).
Figure 5:
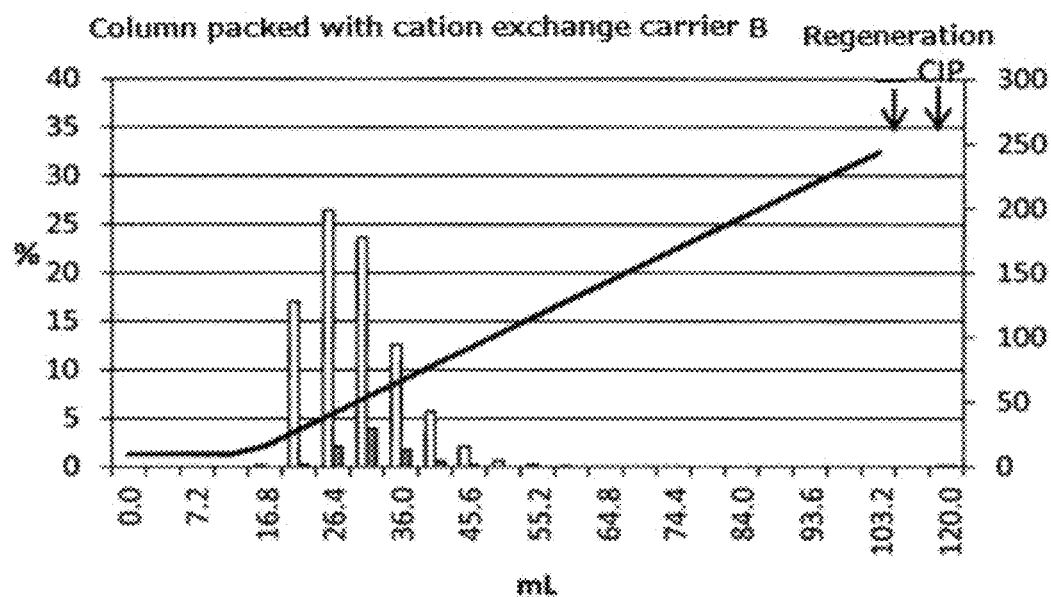
FIG. 5 is a chart showing elution of a monomeric antibody (outline column) and an aggregate of an antibody (hatched column) when a column packed with a carrier having a cation exchange group (cation exchange carrier B) is used. The horizontal axis represents an elution volume (mL), the left vertical axis represents a peak area rate (%), and the right vertical axis represents an ionic strength (mM).
Figure 6:
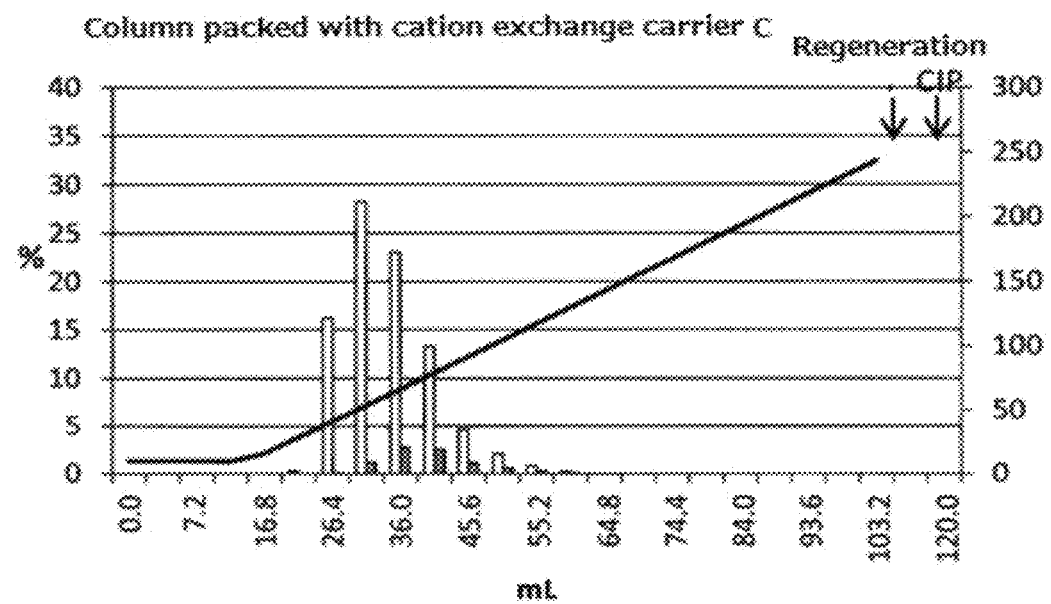
FIG. 6 is a chart showing elution of a monomeric antibody (outline column) and an aggregate of an antibody (hatched column) when a column packed with a carrier having a cation exchange group (cation exchange carrier C) is used. The horizontal axis represents an elution volume (mL), the left vertical axis represents a peak area rate (%), and the right vertical axis represents an ionic strength (mM).
Figure 7:
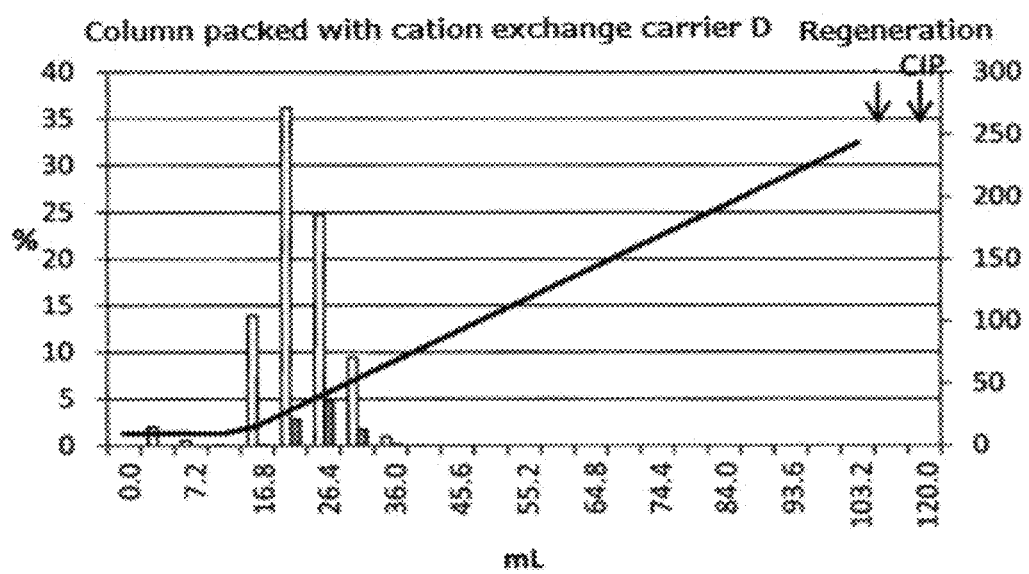
FIG. 7 is a chart showing elution of a monomeric antibody (outline column) and an aggregate of an antibody (hatched column) when a column packed with a carrier having a cation exchange group (cation exchange carrier D) is used. The horizontal axis represents an elution volume (mL), the left vertical axis represents a peak area rate (%), and the right vertical axis represents an ionic strength (mM).

The binding capacity (10% DBC) of each carrier is shown in FIG. 3. As a result, significant difference was not observed in binding capacity of each cation exchange carrier having a carboxyl group as a ligand. Also, no correlation was observed between ion exchange capacity and binding capacity in Table 1. There is a tendency that the lower the pKa, the larger the pH dependency of the binding capacity.

(Measurement of Monomer Content)

Each chromatography eluate was subjected to gel filtration, and aggregates and monomers were fractionated, and the monomer content was determined by comparison of the peak area value. The gel filtration condition is shown below.
Gel Filtration Chromatography Condition
Column: Superdex 200 10/300 GL (ID 1 cm×Height 30 cm) (GE Healthcare)
Flow rate: 0.5 mL/min.
Detection wavelength: 214 nm
Loading solution: 100 µL/Injection (diluted into the range where the absorbance does not exceed 1)
Eluent: PBS (pH 7.4)

Comparative Example 1

Separation of Antibody in Buffer at pH 5 Using Cation Exchange Carrier

A column available from Omnifit (ID 0.66 cm×Height 7 cm) was packed with CM-Sepharose Fast Flow (GE Healthcare), TOYOPEARL CM-650 M (Tosoh Corporation), Fractogel COO (M) (Merck Millipore Corporation), or Glyoxal-COOH (Preparation Example 1) as a cation exchange carrier, and separation was conducted in the following chromatography condition using a human polyclonal antibody (gamma globulin NICHIYAKU: NIHON PHARMACEUTICAL CO., LTD.) prepared into 0.5 mg/mL as a loading solution. To an elution fraction, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Cation Exchange Chromatography Condition
Column: ID 0.66 cm×Height 7 cm, 2.4 mL volume (manufactured by Omnifit Ltd.)
Flow rate: 0.4 mL/min (contact time: 6 minutes) and 0.8 mL/min after CIP
Polyclonal antibody (IgG): gamma globulin NICHIYAKU (NIHON PHARMACEUTICAL CO., LTD.)
Loading solution: 0.5 mg-IgG/mL (10 mM citric acid: pH 5)
Equilibration solution (5 column volume): 10 mM citric acid, pH 5 Loading (30 mg)
Washing solution (5 column volume): 10 mM citric acid, pH 5
Elution gradient (40 column volume): A to B linear gradient
Solution A: 10 mM citric acid, pH 5
Solution B: 250 mM citric acid, pH 5
Regeneration solution (4 column volume): 50 mM citric acid, 250 mM sodium chloride, pH 5
CIP solution (4 column volume): 0.1 M sodium hydroxide, 1 M sodium chloride
Neutralizing and re-equilibrating solution (4 column volume): 10 mM citric acid, pH 5
Fraction: 1 column volume As a result of chromatography of each carrier, separation of the monomer and the aggregate is shown in FIG. 4 to 7, while taking the sum total of the amounts of the monomer and the aggregate in every elution fraction up to the CIP fraction as 100. As a result, the loaded antibody was collected in an elution fraction, and the peak top of the aggregate was slightly deviated from the peak top of the monomer, and gentle separation was confirmed.

Comparative Example 2

Separation of Antibody Using Protein A Carrier

A column available from Omnifit (ID 0.66 cm×Height 7 cm) was packed with MabSelect SuRe (GE healthcare) as a protein A carrier, and separation was conducted in the following chromatography condition using a human polyclonal antibody (gamma globulin NICHIYAKU: NIHON PHARMACEUTICAL CO., LTD.) prepared into 2.5 mg/mL as a loading solution. To an elution fraction, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Protein A Chromatography Condition
Column: ID 0.66 cm×Height 7 cm, 2.4 mL volume (manufactured by Omnifit Ltd.)
Flow rate: 0.4 mL/min (contact time: 6 minutes) and 0.8 mL/min after CIP
Polyclonal antibody (IgG): gamma globulin NICHIYAKU (NIHON PHARMACEUTICAL CO., LTD.)

Loading solution: 2.5 mg-IgG/mL (PBS, pH 7.4)
Equilibration solution (5 column volume): PBS, pH 7.4
Loading (10 mg, 30 mg, or 40 mg)
Washing solution 1 (5 column volume): PBS, pH 7.4
Washing solution 2 (4 column volume): 10 mM Tris/HCl, pH 7
Elution gradient (40 column volume): A to B linear gradient
Solution A: 1 mM citric acid, pH 3.7
Solution B: 250 mM citric acid, pH 3.7
Regeneration solution (4 column volume): 50 mM citric acid, 250 mM sodium chloride, pH 3.7
CIP solution (4 column volume): 0.1 M sodium hydroxide, 1 M sodium chloride
Neutralizing and re-equilibrating solution (4 column volume): PBS, pH 7.4

Figure 8:
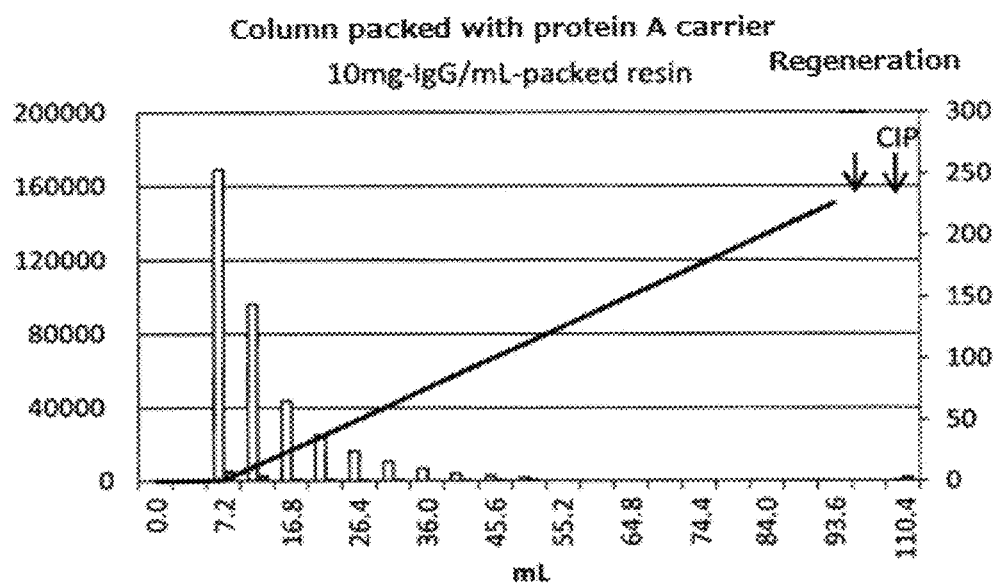
FIG. 8 is a chart showing elution of a monomeric antibody (outline column) and an aggregate of an antibody (hatched column) when a column packed with a carrier having a protein A affinity ligand (protein A carrier) is used and a loading amount of an antibody is 10 mg. The horizontal axis represents an elution volume (mL), the left vertical axis represents a peak area value, and the right vertical axis represents an ionic strength (mM).
Figure 9:
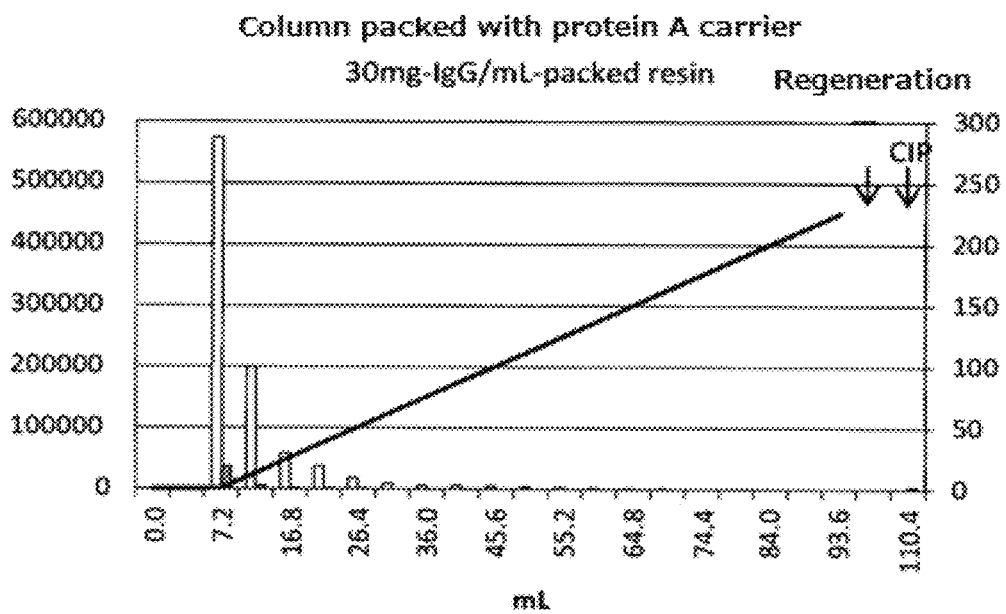
FIG. 9 is a chart showing elution of a monomeric antibody (outline column) and an aggregate of an antibody (hatched column) when a column packed with a carrier having a protein A affinity ligand (protein A carrier) is used and a loading amount of an antibody is 30 mg. The horizontal axis represents an elution volume (mL), the left vertical axis represents a peak area value, and the right vertical axis represents an ionic strength (mM).
Figure 10:
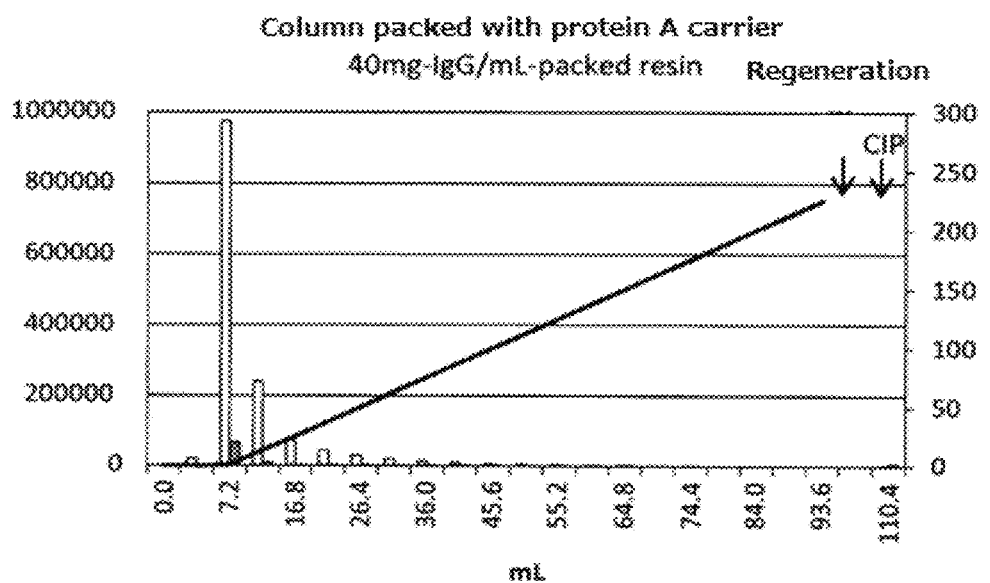
FIG. 10 is a chart showing elution of a monomeric antibody (outline column) and an aggregate of an antibody (hatched column) when a column packed with a carrier having a protein A affinity ligand (protein A carrier) is used and a loading amount of an antibody is 40 mg. The horizontal axis represents an elution volume (mL), the left vertical axis represents a peak area value, and the right vertical axis represents an ionic strength (mM).

As a result of each chromatography, area values of the monomer and the aggregate in each fraction up to the CIP fraction are shown in FIG. 8 to 10. As a result, while the loaded antibody was collected in an elution fraction, the peak top of the aggregate was eluted in an initial stage together with the monomer peak, and separation of the aggregate was not observed with any loading amount. The binding capacity (10% DBC) of the protein A carrier was approximately 50.3 mg/mL.

Comparative Example 3

Separation of Antibody Using Integrated Column in which Column Packed with Protein A Carrier and Column Packed with Cation Exchange Carrier Having Sulfopropyl Group as Ligand (SP-Sepharose Fast Flow) are Connected Columns available from Omnifit (ID 0.66 cm×Height 7 cm) were respectively packed with MabSelect SuRe (GE Healthcare) as a protein A carrier and SP-Sepharose Fast Flow Flow (GE Healthcare) as a cation exchange carrier, the two columns were connected in the order of the column packed with the protein A carrier and the column packed with the cation exchange carrier, and a chromatography operation was conducted as a single column.

Separation was conducted in the following chromatography condition using a human polyclonal antibody (gamma globulin NICHIYAKU: NIHON PHARMACEUTICAL CO., LTD.) prepared into 2.5 mg/mL as a loading solution. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.
Connecting Column Chromatography Condition
Column: connecting body composed of columns of ID 0.66 cm×Height 7 cm, 2.4 mL volume (manufactured by Omnifit Ltd.)
Flow rate: 0.4 mL/min (contact time: 6 minutes) and 0.8 mL/min after CIP
Polyclonal antibody (IgG): gamma globulin NICHIYAKU (NIHON PHARMACEUTICAL CO., LTD.)
Loading solution: 2.5 mg-IgG/mL (PBS, pH 7.4; 10 mM phosphoric acid, 150 mM sodium chloride and the like)
Equilibration solution (5 column volume): PBS, pH 7.4
Loading: (40 mg)
Washing solution 1 (5 column volume): PBS, pH 7.4
Washing solution 2 (4 column volume): 10 mM Tris/HCl, pH 7
Elution gradient (40 column volume): A to B linear gradient
Solution A: 1 mM citric acid, pH 3.7
Solution B: 250 mM citric acid, pH 3.7
Regeneration solution (4 column volume): 50 mM citric acid, 250 mM sodium chloride, pH 3.7
CIP solution (4 column volume): 0.1 M sodium hydroxide, 1 M sodium chloride
Neutralizing and re-equilibrating solution (4 column volume): PBS, pH 7.4

Figure 11:
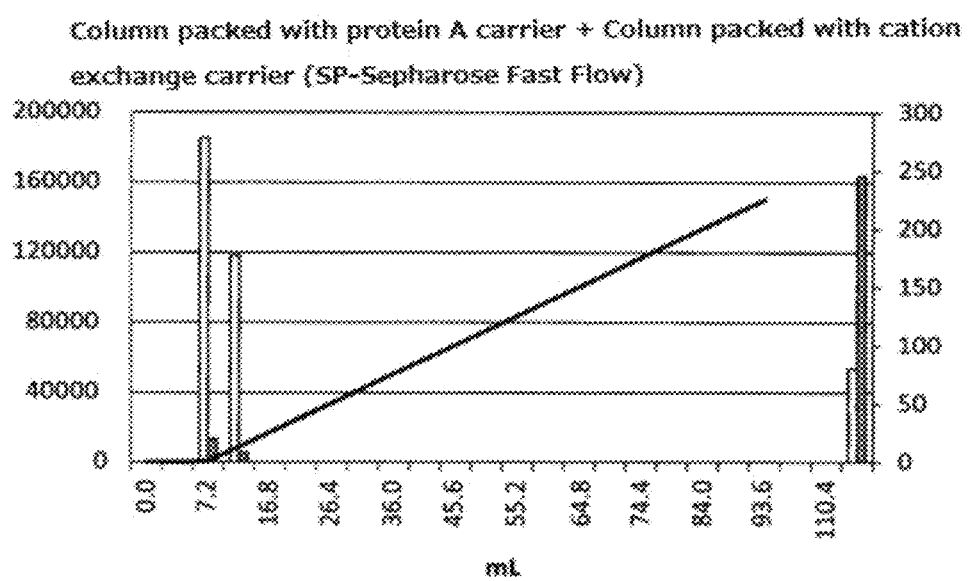
FIG. 11 is a chart showing elution of a monomeric antibody (outline column) and an aggregate of an antibody (hatched column) when a column packed with a carrier having a protein A affinity ligand (protein A carrier) is directly connected to a column packed with a carrier having a cation exchange group (SP-Sepharose Fast Flow) such that the column packed with a carrier having a protein A affinity ligand is upstream. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 11. At this time, when the monomer amount in the elution fraction of the 40 mg antibody loading test in Comparative Example 2 is taken as 100, the monomer collected up to the regeneration fraction in Comparative Example 3 was 21.0%, and the monomer content was 94.1%. The monomer collected up to the CIP fraction was 22.9%, and the recovery of the monomer that could be eluted by ionic strength was poor when the column packed with the cation exchange carrier having a sulfopropyl group as a ligand was connected to the column packed with the protein A carrier.

Reference Example 1

Separation of Antibody Using Integrated Column in which Column Packed with Protein A Carrier and Column Packed with Cation Exchange Carrier a Having Carboxyl Group and pKa of Less than 4.0 as Ligand (CM-Sepharose Fast Flow) are Connected Columns available from Omnifit (ID 0.66 cm×Height 7 cm) were respectively packed with MabSelect SuRe (GE Healthcare) as a protein A carrier and CM-Sepharose Fast Flow (GE Healthcare) as a cation exchange carrier A, the two columns were connected in the order of the column packed with the protein A carrier and the column packed with the cation exchange carrier A, and a chromatography operation was conducted as a single column. Separation was conducted in the chromatography condition of Comparative Example 3 using a human polyclonal antibody (gamma globulin NICHIYAKU: NIHON PHARMACEUTICAL CO., LTD.) prepared into 2.5 mg/mL as a loading solution. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.
Connecting Column Chromatography Condition
Column: connecting body composed of columns of ID 0.66 cm×Height 7 cm, 2.4 mL volume (manufactured by Omnifit Ltd.)
Flow rate: 0.4 mL/min (contact time: 6 minutes) and 0.8 mL/min after CIP
Polyclonal antibody (IgG): gamma globulin NICHIYAKU (NIHON PHARMACEUTICAL CO., LTD.)
Loading solution: 2.5 mg-IgG/mL (PBS, pH 7.4; 10 mM phosphoric acid, 150 mM sodium chloride and the like)
Equilibration solution (5 column volume): PBS, pH 7.4
Loading: (40 mg)
Washing solution 1 (5 column volume): PBS, pH 7.4
Washing solution 2 (4 column volume): 10 mM Tris/HCl, pH 7
Elution gradient (40 column volume): A to B linear gradient Solution A: 1 mM citric acid, pH 3.7
Solution B: 250 mM citric acid, pH 3.7
Regeneration solution (4 column volume): 50 mM citric acid, 250 mM sodium chloride, pH 3.7
CIP solution (4 column volume): 0.1 M sodium hydroxide, 1 M sodium chloride
Neutralizing and re-equilibrating solution (4 column volume): PBS, pH 7.4

Figure 12:
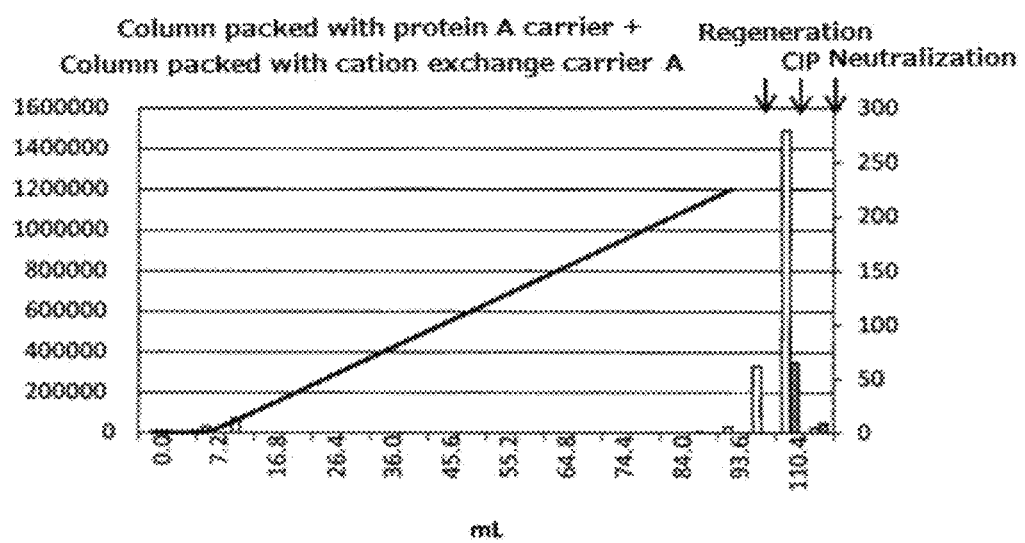
FIG. 12 is a chart showing elution of a monomeric antibody (outline column) and an aggregate of an antibody (hatched column) when a column packed with a carrier having a protein A affinity ligand (protein A carrier) is directly connected to a column packed with a carrier having a cation exchange group (cation exchange carrier A) such that the column packed with a carrier having a protein A affinity ligand is upstream. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 12. At this time, when the monomer amount in the elution fraction of the 40 mg antibody loading test in Comparative Example 2 is taken as 100, the monomer collected up to the regeneration fraction in Reference Example 1 was 21.2%, and the monomer content was 99.0%. The monomer collected up to the CIP fraction was 73.7%, and the monomer content was 83.3%. The recovery of the monomer that could be eluted by ionic strength was poor when the column packed with the cation exchange carrier A having a carboxyl group and pKa of less than 4.0 as a ligand was connected to the column packed with the protein A carrier.

Example 1

Separation of Antibody Using Integrated Column in which Column Packed with Protein A Carrier and Column Packed with Cation Exchange Carrier B Having Carboxyl Group (TOYOPEARL CM-650 M) as Ligand are Connected Columns available from Omnifit (ID 0.66 cm×Height 7 cm) were respectively packed with MabSelect SuRe (GE Healthcare) as a protein A carrier and TOYOPEARL CM-650 M (Tosoh Corporation) as a cation exchange carrier B, the two columns were connected in the order of the column packed with the protein A carrier and the column packed with the cation exchange carrier B, and the chromatography operation was conducted as a single column. Separation was conducted in the chromatography condition of Comparative Example 3 using a human polyclonal antibody (gamma globulin NICHIYAKU: NIHON PHARMACEUTICAL CO., LTD) prepared into 2.5 mg/mL as a loading solution. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Figure 13:
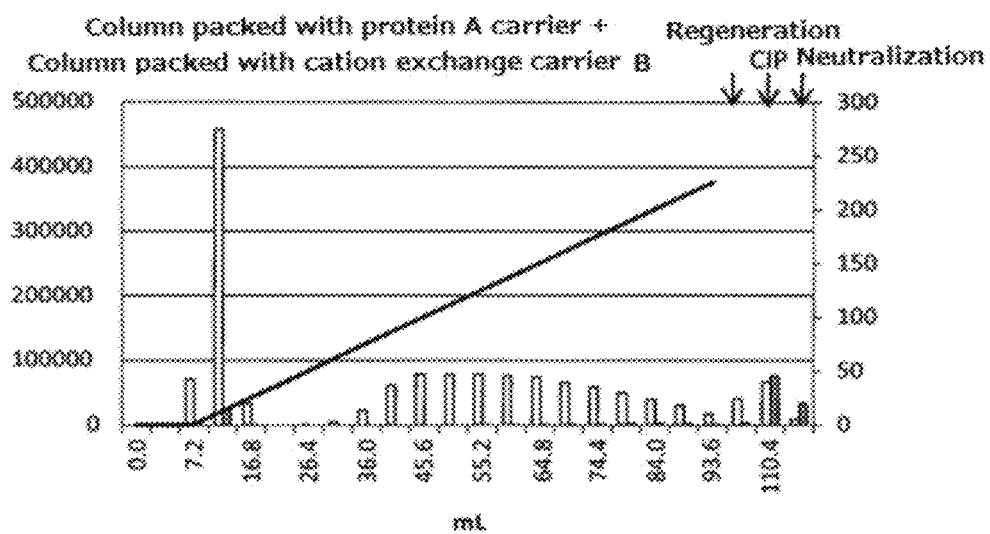
FIG. 13 is a chart showing elution of a monomer antibody (outline column) and an aggregate of an antibody (hatched column) when a column packed with a carrier having a protein A affinity ligand (protein A carrier) is directly connected to a column packed with a carrier having a cation exchange group (cation exchange carrier B) such that the column packed with a carrier having a protein A affinity ligand is upstream. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 13. At this time, when the monomer amount in the elution fraction of the 40 mg antibody loading test in Comparative Example 2 of the same loading amount is taken as 100, the monomer collected up to the regeneration fraction in Example 1 was 91.6%, and the monomer content was 96.7%.

Regarding the evaluation result of each of the connecting columns in Table 2, the monomer recovery up to the regeneration fraction, the monomer content in the mixture up to the regeneration fraction, and the monomer content in the eluate mixture up to the monomer recovery of 80% are shown in comparison with Comparative Example 2. The monomer recovered up to the regeneration fraction in Comparative Example 2 was 99.9%, and the monomer content was 93.5%. Also in comparison at the point of time when the monomer recovery was 80%, the monomer content in Comparative Example 2 was 93.4%, and in contrast, the monomer content in Example 1 was 97.1% and the monomer content increased.

Example 2

Separation of Antibody Using Integrated Column in which Column Packed with Protein A Carrier and Column Packed with Cation Exchange Carrier C Having Carboxyl Group (Fractogel COO(M)) as Ligand are Connected Columns available from Omnifit (ID 0.66 cm×Height 7 cm) were respectively packed with MabSelect SuRe (GE Healthcare) as a protein A carrier and Fractogel COO(M) (Merck) as a cation exchange carrier C, the two columns were connected in the order of the column packed with the protein A carrier and the column packed with the cation exchange carrier C, and the chromatography operation was conducted as a single column. Separation was conducted in the chromatography condition of Comparative Example 3 using a human polyclonal antibody (gamma globulin NICHIYAKU: NIHON PHARMACEUTICAL CO., LTD) prepared into 2.5 mg/mL as a loading solution. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Figure 14:
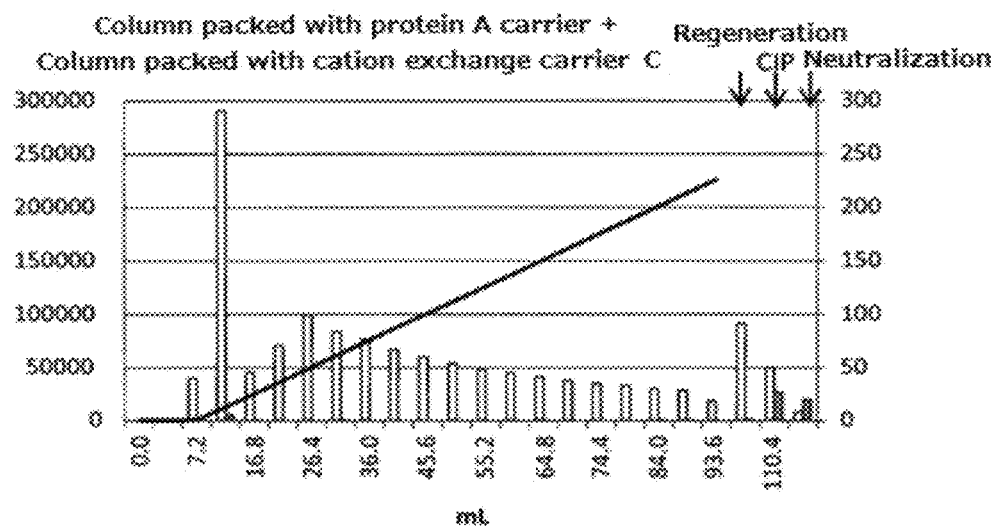
FIG. 14 is a chart showing elution of a monomeric antibody (outline column) and an aggregate of an antibody (hatched column) when a column packed with a carrier having a protein A affinity ligand (protein A carrier) is directly connected to a column packed with a carrier having a cation exchange group (cation exchange carrier C) such that the column packed with a carrier having a protein A affinity ligand is upstream. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 14. At this time, when the monomer amount in the elution fraction of the 40 mg antibody loading test in Comparative Example 2 is taken as 100, the monomer collected up to the regeneration fraction in Example 2 was 86.7%, and the monomer content was 99.2%.

Regarding the evaluation result of each of the connecting columns in Table 2, the monomer recovery up to the regeneration fraction, the monomer content in the mixture up to the regeneration fraction, and the monomer content in the eluate mixture up to the monomer recovery of 80% are shown in comparison with Comparative Example 2. The monomer recovered up to the regeneration fraction in Comparative Example 2 was 99.9%, and the monomer content was 93.5%. Also in comparison at the point of time when the monomer recovery was 80%, the monomer content in Comparative Example 2 was 93.4%, and in contrast, the monomer content in Example 2 was 99.2% and the monomer content increased.

Example 3

Separation of Antibody Using Integrated Column in which Column Packed with Protein a Carrier and Column Packed with Cation Exchange Carrier D Having Carboxyl Group (Glyoxal-COOH) as Ligand are Connected Columns available from Omnifit (ID 0.66 cm×Height 7 cm) were respectively packed with MabSelect SuRe (GE Healthcare) as a protein A carrier and Glyoxal-COOH as a cation exchange carrier D, the two columns were connected in the order of the column packed with the protein A carrier and the column packed with the cation exchange carrier D, and the chromatography operation was conducted as a single column. Separation was conducted in the chromatography condition of Comparative Example 3 using a human polyclonal antibody (gamma globulin NICHIYAKU: NIHON PHARMACEUTICAL CO., LTD) prepared into 2.5 mg/mL as a loading solution. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Figure 15:
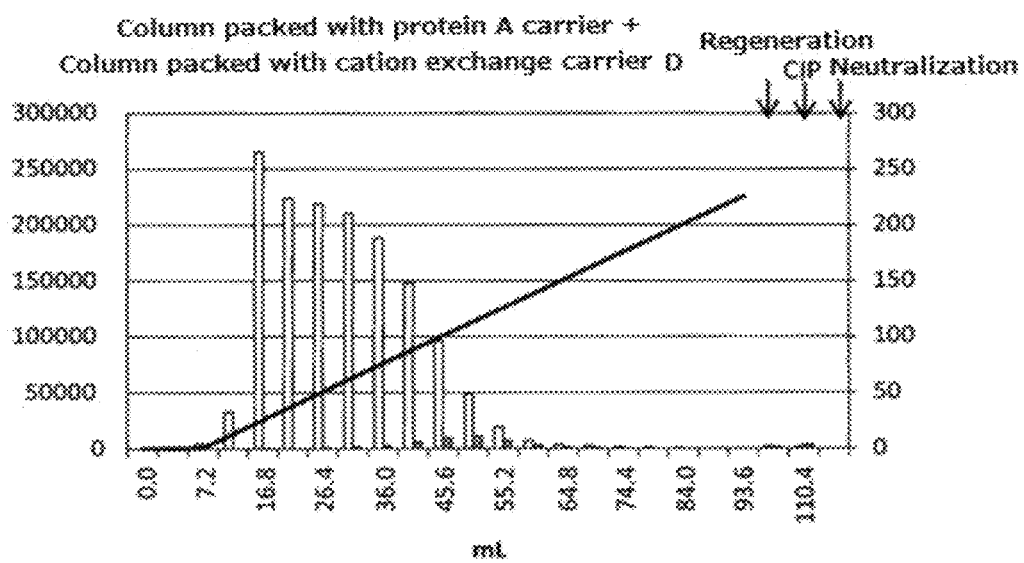
FIG. 15 is a chart showing elution of a monomeric antibody (outline column) and an aggregate of an antibody (hatched column) when a column packed with a carrier having a protein A affinity ligand (protein A carrier) is directly connected to a column packed with a carrier having a cation exchange group (cation exchange carrier D) such that the column packed with a carrier having a protein A affinity ligand is upstream. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 15. At this time, when the monomer amount in the elution fraction of the 40 mg antibody loading test in Comparative Example 2 is taken as 100, the monomer collected up to the regeneration fraction in Example 3 was 102.0%, and the monomer content was 96.7%. The recovery more than 100% may result from the error of injected amount at the time of gel filtration, and the comparison of the monomer content relative to Comparative Example had no problem from the view of the separation behavior of the monomer and aggregate of FIG. 15.

Regarding the evaluation result of each of the connecting columns in Table 2, the monomer recovery up to the regeneration fraction, the monomer content in the mixture up to the regeneration fraction, and the monomer content in the eluate mixture up to the monomer recovery of 80% are shown in comparison with Comparative Example 2. The monomer recovered up to the regeneration fraction in Comparative Example 2 was 99.9%, and the monomer content was 93.5%. Also in comparison at the point of time when the monomer recovery was 80%, the monomer content in Comparative Example 2 was 93.4%, and in contrast, the monomer content in Example 3 was 99.1% and the monomer content increased.

Example 4

Separation of Antibody Using Mixed Column in which Protein A Carrier and Cation Exchange Carrier D Having Carboxyl Group (Glyoxal-COOH) as Ligand are Mixed and Packed in One Column Column available from Omnifit (ID 0.66 cm×Height 7 cm) was packed with MabSelect SuRe (GE Healthcare) as a protein A carrier and Glyoxal-COOH as a cation exchange carrier D at the state of the mixture in the volume ratio of 4:1. Separation was conducted in the chromatography condition of Comparative Example 2 using a human polyclonal antibody (gamma globulin NICHIYAKU: NIHON PHARMACEUTICAL CO., LTD) prepared into 2.5 mg/mL as a loading solution. The loaded amount of the antibody was 10 mg. The operation was conducted with a single column volume of 2.4 mL per one column. To an eluate, arginine was added in a final concentration of 50 to 100 mM, and the monomer content was measured by gel filtration chromatography at pH 5 to 6. Also, the amounts of the monomer and the aggregate in each fraction were determined by the peak area value analysis.

Figure 16:
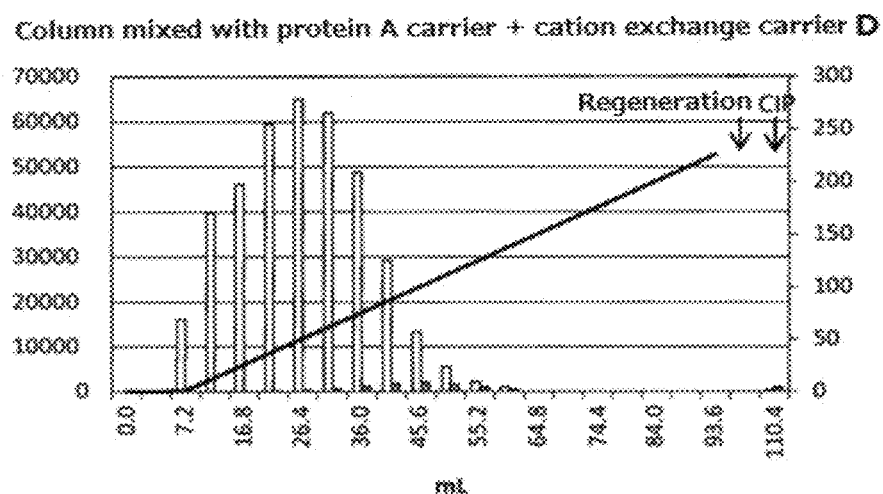
FIG. 16 is a chart showing elution of a monomeric antibody (outline column) and an aggregate of an antibody (hatched column) when a carrier having a protein A affinity ligand (protein A carrier), and a carrier having a cation exchange group (cation exchange carrier D) are mixed in the same column. The horizontal axis represents an elution volume (mL), the left vertical axis represents a peak area value, and the right vertical axis represents an ionic strength (mM).

As a result of chromatography, area values of the monomer and the aggregate of each fraction up to the CIP fraction are shown in FIG. 16. At this time, when the monomer amount in the elution fraction of the 10 mg antibody loading test in Comparative Example 2 is taken as 100, the monomer collected up to the regeneration fraction in Example 4 was 103.0%, and the monomer content was 97.3%. The recovery more than 100% may result from the error of injected amount at the time of gel filtration, and the comparison of the monomer content relative to Comparative Example had no problem from the view of the separation behavior of the monomer and aggregate of FIG. 16.

Regarding the evaluation result of the mixed column in Table 3, the monomer recovery up to the regeneration fraction, the monomer content in the mixture up to the regeneration fraction, and the monomer content in the eluate mixture up to the monomer recovery of 80% are shown in comparison with Comparative Example 2. The monomer recovered up to the regeneration fraction in Comparative Example 2 was 99.9%, and the monomer content was 96.5%. Also in comparison at the point of time when the monomer recovery was 80%, the monomer content in Comparative Example 2 was 97.1%, and in contrast, the monomer content in Example 4 was 99.1% and the monomer content increased.

TABLE 2

|  | Column packed with protein A carrier (Comparative Example 2) | Integrated column of column packed with protein A carrier and column packed with cation exchange carrier B (Example 1) | Integrated column of column packed with protein A carrier and column packed with cation exchange carrier C (Example 2) | Integrated column of column packed with protein A carrier and and column packed with cation exchange carrier D (Example 3) |
|---|---|---|---|---|
| Monomer yield up to regeneration fraction | 99.9% | 91.6% | 86.7% | 102.0% |
| Monomer content up to regeneration fraction | 93.5% | 96.7% | 99.2% | 96.7% |
| Monomer content up to 80% monomer yield | 93.4% | 97.1% | 99.2% | 99.1% |

TABLE 3

|  | Column packed with protein A carrier (Comparative Example 2) | Mixed column of protein A carrier and cation exchange carrier D (Example 4) |
|---|---|---|
| Monomer yield up to regeneration fraction | 99.9% | 103.0% |
| Monomer content up to regeneration fraction | 96.5% | 97.3% |
| Monomer content up to 80% monomer yield | 97.1% | 99.1% |

As described above, according to the first embodiment of the present invention, a novel separation mode and a use method capable of achieving high recovery of 80% or more or capable of improving the monomer content even if the recovery is not 80% or more are provided by the method for purifying an antibody and the like in which an affinity carrier and a cation exchange carrier are used to prepare an integrated column 1 connecting a column containing the affinity carrier and a column containing the cation exchange carrier or a column 2 having a mixture of the affinity carrier and the cation exchange carrier, the antibody and the like is adsorbed on the column 1 or the column 2, and then the adsorbed antibody and the like is eluted from the column 1 or the column 2. This contributes to improvement in productivity of the production process and high purity of antibody drug.

In addition, according to the second embodiment of the present invention, when the cation exchange carrier having pKa of 4.0 or more was subjected to ionic strength-dependent elution in an acidic solution at pH 4.0 or less used in affinity chromatography elution, it was possible to improve the monomer content at an antibody recovery of 80% or more. Also according to the second embodiment of the present invention, it is not necessary to temporarily collect the eluate of the protein A carrier, and an integrated column 1 connecting a column containing the affinity carrier and a column containing the cation exchange carrier or a column 2 having a mixture of the affinity carrier and the cation exchange carrier can be prepared to adsorb the antibody and the like on the column 1 or the column 2, and to elute the adsorbed antibody and the like from the column 1 or the column 2.

That is, by the use method of the second embodiment of the present invention, an antibody and the like is separated from the cation exchange carrier at acidic elution pH in which a target molecule is eluted from the affinity carrier, or an affinity carrier and a cation exchange carrier are used to prepare an integrated column 1 connecting a column containing the affinity carrier and a column containing the cation exchange carrier or a column 2 having a mixture of the affinity carrier and the cation exchange carrier, the antibody and the like is adsorbed on the column 1 or the column 2, and then the adsorbed antibody and the like is eluted from the column 1 or the column 2. Thus, it is possible to contribute to improvement in productivity of the production process and high purity of antibody drug.

The invention claimed is:

1. A method for purifying a target substance, the method comprising:
    applying a solution containing the target substance to a column, wherein the column comprises a first carrier comprising an affinity ligand which has affinity to the target substance and a second carrier comprising a cation exchange group;
    passing an elution solution through the column, thereby eluting the target substance,
    wherein the target substance is immunoglobulin G, an immunoglobulin G derivative, a Fc-containing molecule, Fab, scFv, a diabody, or a molecule containing a binding part capable of binding to an antigen,
    wherein the column is an integrated column having a first column having the first carrier and a second column having the second carrier, or a single column having a mixture of the first carrier and the second carrier,
    wherein the first column is connected to the second column such that the second column is positioned downstream of the first column,
    wherein the applying and the passing are carried out from upstream to downstream of the integrated column or the single column,
    wherein affinity chromatography and cation exchange chromatography are performed at one chromatography step, and
    wherein a pKa of the cation exchange group is equal or greater than a pH of the elution solution, and the pKa of the cation exchange group is 4.0 or more and the pH of the elution solution is 4.0 or less.

2. The method according to claim 1, wherein the eluting of the target substance comprises eluting the target substance by the elution solution and continuously changing an ionic strength of the elution solution.

3. The method according to claim 1, wherein the eluting of the target substance comprises eluting the target substance by the elution solution and stepwise changing an ionic strength of the elution solution.

4. The method according to claim 1, further comprising:
    equilibrating the column with an equilibration buffer; and
    washing the column with a wash buffer having a pH higher than a pH of the elution solution and an ionic strength lower than an ionic strength of the equilibration buffer and an ionic strength of the solution containing the target substance, before the passing of the elution solution through the column.

5. The method according to claim 1, further comprising:
    equilibrating the column with an equilibration buffer;
    washing the column with a first wash buffer having a pH higher than a pH of the elution solution and an ionic strength greater than or equal to an ionic strength of the equilibration buffer and an ionic strength of the solution containing the target substance; and
    further washing the column with a second wash buffer having a pH higher than a pH of the elution solution and an ionic strength lower than an ionic an strength of the equilibration buffer and an ionic an strength of the solution containing the target substance, before the passing of the elution solution through the column.

6. The method according to claim 1, wherein the first carrier comprises a ligand comprising protein A, protein G, protein L, or an analog thereof.

7. The method according to claim 1, wherein the first carrier comprises a ligand comprising protein A or an analog thereof.

8. The method according to claim 1, wherein the second carrier comprises a ligand comprising a carboxyl group.

9. The method according to claim 8, wherein the carboxyl group is a carboxyl group of an acidic amino acid.

10. The method according to claim 1, wherein the first carrier has a binding capacity represented by $DBC_{10\%}$ of from 1 mg/mL to 100 mg/mL with respect to IgG in a contact time of 6 minutes.

11. The method according to claim 1, wherein the second carrier has an ion exchange capacity of from 0.001 mmol/mL to 0.5 mmol/mL.

12. The method according to claim 1, wherein the first carrier has a volume average particle diameter of from 1 μm to 1000 μm, and the second carrier has a volume average particle diameter of from 1 μm to 1000 μm.

13. The method according to claim 1, wherein
    the second carrier comprises a cation exchange group comprising a carboxyl group-containing ligand, wherein the carboxyl group-containing ligand has a pKa of 4.0 or more, wherein the elution solution comprises
    an acidic buffer having a pH of 4.0 or less.

14. The method according to claim 1, wherein the second carrier has a binding capacity represented by $DBC_{10\%}$ of from 1 mg/mL to 200 mg/mL with respect to IgG in a contact time of 6 minutes.

15. The method according to claim 1, wherein
the column is an integrated column comprising a first column comprising the first carrier and a second column comprising the second carrier,
the applying of the solution to the column is conducted at a neutral pH, and
the passing of the elution solution comprises passing an acidic buffer having a pH of 4.0 or less through the column such that the target substance is eluted.

16. The method according to claim 1, wherein the column is an integrated column comprising a first column comprising the first carrier and a second column comprising the second carrier, and a volume ratio of the first carrier to the second carrier is from 1/20 to 20/1.

17. The method according to claim 1, wherein
the column is a single column comprising a mixture of the first carrier and the second carrier,
the applying of the solution to the column is conducted at a neutral pH, and
the passing of the elution solution comprises passing an acidic buffer having a pH of 4.0 or less through the column such that the target substance is eluted.

18. The method according to claim 1, wherein the column is a single column comprising a mixture of the first carrier and the second carrier, and a volume ratio of the first carrier to the second carrier is from 1/20 to 20/1.

19. The method according to claim 1, wherein a ratio of a binding capacity of the first carrier represented by $DBC_{10\%}$ to a binding capacity of the second carrier represented by $DBC_{10\%}$ is from 1/10 to 10/1, and
wherein the binding capacities of the first and second carriers represented by $DBC_{10\%}$ are binding capacities of the first and second carriers with respect to IgG in a contact time of 6 minutes, respectively.

20. The method according to claim 1, wherein the first carrier does not have a cation exchange group, and the second carrier does not have an affinity ligand having affinity with the target substance.

21. The method according to claim 1, wherein the column is an integrated column comprising a first column comprising the first carrier and a second column comprising the second carrier, wherein the first carrier does not have a cation exchange group, and the second carrier does not have an affinity ligand having affinity with the target substance.

* * * * *